US012582443B2

(12) United States Patent
    Wang

(10) Patent No.: US 12,582,443 B2
(45) Date of Patent: Mar. 24, 2026

(54) FETAL INTRAUTERINE POSITIONING FIXATION DEVICE AND SYSTEM THEREOF

(71) Applicant: Xiamen Brana Design Co., Ltd., Xiamen (CN)

(72) Inventor: Zhongtang Wang, Xiamen (CN)

(73) Assignee: Xiamen Brana Design Co., Ltd., Xiamen (CN)

( * ) Notice: Subject to any disclaimer, the term of this patent is extended or adjusted under 35 U.S.C. 154(b) by 592 days.

(21) Appl. No.: 18/092,341

(22) Filed: Jan. 1, 2023

(65) Prior Publication Data
    US 2023/0210561 A1      Jul. 6, 2023

(30) Foreign Application Priority Data

Jan. 1, 2022    (CN) .......................... 202210000011.4

(51) Int. Cl.
    *A61B 17/44*        (2006.01)
    *A61B 17/00*        (2006.01)
    *A61B 17/30*        (2006.01)
    *A61B 34/00*        (2016.01)
            (Continued)

(52) U.S. Cl.
    CPC .............. *A61B 17/44* (2013.01); *A61B 34/71* (2016.02); *A61B 2017/00296* (2013.01); *A61B 2017/00486* (2013.01); *A61B 2017/00557* (2013.01); *A61B 2017/308* (2013.01);
            (Continued)

(58) Field of Classification Search
    CPC ..... A61B 17/42; A61B 17/4241; A61B 17/44; A61B 2017/00296; A61B 2017/003; A61B 2017/00305; A61B 2017/00314;

A61B 2017/00318; A61B 2017/00323; A61B 2017/00327; A61B 2017/0034; A61B 2017/00486; A61B 2017/00557; A61B 2017/306; A61B 2017/308; A61B 2017/445; A61B 2017/447; A61B 34/30; A61B 34/70; A61B 34/71; A61B 34/74; A61B 2034/2048; A61B 2034/301; A61B 2034/302; A61B 2034/303;
            (Continued)

(56)                References Cited

U.S. PATENT DOCUMENTS 6,641,575  B1 *  11/2003  Lonky ................ A61B 17/0218
                                                            600/210
2019/0000574  A1 *   1/2019  Cohen .................... A61B 90/50
2023/0074350  A1 *   3/2023  Scheib ................... A61B 34/30

* cited by examiner

*Primary Examiner* — Robert A Lynch
(74) *Attorney, Agent, or Firm* — David & Raymond Patent Firm; Raymond Y Chan

(57)                ABSTRACT

A fetal intrauterine positioning fixation device is configured for entering an amniotic cavity through a vaginal cervical fetal membrane access and/or abdominal wall uterine fetal membrane access to adjust and fix a fetal position in a maternal uterus. The fetal intrauterine positioning fixation device includes a manipulator, a mechanical arm and a surgical robot, the manipulator and mechanical arm can enter an amniotic cavity through a vaginal cervical fetal membrane channel or abdominal wall uterine fetal membrane channel, so that a doctor can control the manipulator and mechanical arm through the surgical robot or a handle to identify a fetus, adjust a fetal position and fix the fetus according to a preoperative planning, and monitor a fetal status in real time, expose a surgical treatment area, and create an operation space for implementing intrauterine fetal surgery.

14 Claims, 19 Drawing Sheets

(51)  Int. Cl.
     *A61B 34/20*       (2016.01)
     *A61B 34/30*       (2016.01)
(52)  U.S. Cl.
     CPC . *A61B 2034/2048* (2016.02); *A61B 2034/302*
              (2016.02); *A61B 2034/305* (2016.02)
(58)  Field of Classification Search
     CPC ........ A61B 2034/304; A61B 2034/305; A61B
                                2034/306
     See application file for complete search history.

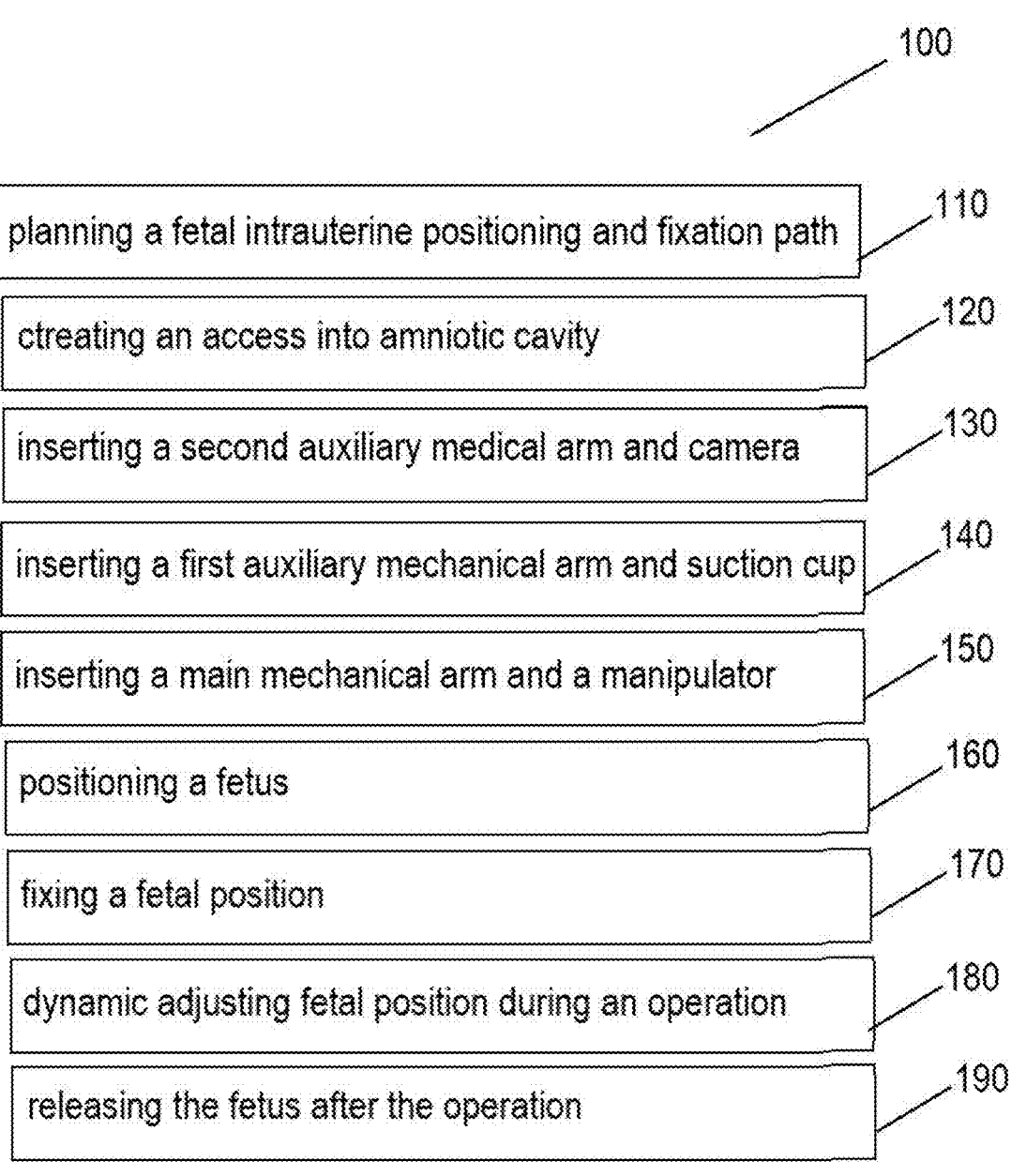

100 planning a fetal intrauterine positioning and fixation path — 110 ctreating an access into amniotic cavity — 120 inserting a second auxiliary medical arm and camera — 130 inserting a first auxiliary mechanical arm and suction cup — 140 inserting a main mechanical arm and a manipulator — 150 positioning a fetus — 160 fixing a fetal position — 170 dynamic adjusting fetal position during an operation — 180 releasing the fetus after the operation — 190

FIG. 33

FETAL INTRAUTERINE POSITIONING FIXATION DEVICE AND SYSTEM THEREOF

CROSS REFERENCE OF RELATED APPLICATION

This application is a non-provisional application that claims the benefit of priority under 35 U.S.C. § 119(e) to a Chinese application, application number 202210000011.4, filed Jan. 1, 2022, which is incorporated herewith by reference in its entirety.

BACKGROUND OF THE PRESENT INVENTION

Field of Invention

The present invention relates to a field of a medical device, in particular to a fetal intrauterine positioning and fixing manipulator, mechanical arm, surgical robot and system thereof.

Description of Related Arts

Fetal birth defects have become an important global public health and social problem. A clinical data of the past 30 years shows that a result of fetal surgery to correct birth defects is not satisfactory, because it is difficult to avoid damaging a uterus and a placenta, and fetal separation from a uterus and amniotic fluid environment, resulting in placental abruption, maternal uterine contraction, premature delivery, fetal death, and uterine rupture after surgery.

A vaginal cervical amniotic cavity channel kit (Chinese patent application No. 202111426867. X) and/or abdominal uterine amniotic cavity channel device (Chinese patent application No. 202111426866.5) are used to establish an intrauterine surgical pathway through a natural cavity or abdominal wall wound. Then a minimally invasive surgery can be performed by a surgical robot, which can avoid damaging a mother uterus and placenta, and also ensure that a fetus does not need to leave the mother uterine amniotic fluid environment during an operation. However, a small month fetus floats in a maternal uterus amniotic fluid, and a large month fetus enters a pelvis, resulting in limited mobility of the fetus. In particular, a surgical field may deviate from an established surgical access, which makes robot minimally invasive surgery extremely difficult. Therefore, it is urgent to adjust and fix the fetus position in the mother uterus, fully expose a vision of the surgical field, build a surgical operation space, and create conditions for a minimally invasive intrauterine fetal surgery by the surgical robot, so as to expand a scope of intrauterine fetal surgery.

SUMMARY OF THE PRESENT INVENTION

The invention is advantageous in that it provides a fetal intrauterine positioning and fixing manipulator, mechanical arm, surgical robot and system. A surgical robot or a doctor can manipulate the mechanical arm and manipulator to adjust the fetal intrauterine position, fix the fetus, and expose a surgical treatment field according to a preoperative planning, so as to build an operating space for safe and accurate intrauterine fetal surgery.

According to the present invention, the foregoing and other objects and advantages are attained by a fetal intrauterine positioning and fixing manipulator, which comprises a wrist joint, a first finger and a second finger. A proximal end of the wrist joint is connected with a mechanical arm through a transmission, and a distal end of the wrist joint is fixedly connected with a finger wrist joint axis for flexing, extending and rotating the finger wrist joint. A proximal end of the finger wrist joint is connected with the mechanical arm through a wire rope threaded through the wrist joint, and a distal end of the finger wrist joint is detachably connected with the first finger and the second finger respectively. A proximal end of the first finger is detachably connected with the distal end of the first finger wrist joint to cooperate with the second finger to clamp or hold a fetal body or limb. A proximal end of the second finger is detachably connected with the distal end of the second finger wrist joint, which is configured to cooperate with the first finger to clamp or hold the fetal body and/or limb.

Preferably, the proximal end of the wrist joint is provided with a first flange, a distal end of the first flange is connected with the wrist joint by sliding and rotating, a proximal end of the first flange is fixedly connected with an outer sleeve of the mechanical arm, and is connected with a power device of the surgical robot through a steel wire rope threaded through the mechanical arm.

Preferably, the first finger comprises a first arc rod, a first connecting tube, a first wrist joint, a first pull rod and a second pull rod, wherein the first arc rod can be detachably connected with the first connecting tube, the first connecting tube, the first pull rod and the second pull rod can rotate axially around the first wrist joint, and the first connecting tube, the first pull rod and the second pull rod are fixedly connected with each other.

Preferably, the second finger comprises a second arc rod, a second connecting tube, a second finger wrist joint, a third pull rod and a fourth pull rod, wherein the second arc rod can be detachably connected with the second connecting tube, the second connecting tube, the third pull rod and the fourth pull rod can rotate axially around the second finger wrist joint, and the second connecting tube, the third pull rod and the fourth pull rod are fixedly connected with each other.

Preferably, the first finger and the second finger are combined and connected to clamp or hold the fetal body and/or limb. The first arc rod and an inner arc of the second arc rod are arranged relatively. The first pull rod is connected with the surgical robot power device through the first wire rope, the third pull rod is connected with the surgical robot power device through the second wire rope, and the second pull rod and the fourth pull rod are connected with an elastic strip.

Preferably, the first finger and the second finger are combined and connected to clamp or hold the fetal body or limb. The first arc rod and an inner arc of the second arc rod are arranged in a relative manner. The first pull rod and the third pull rod are connected with the surgical robot power device through a shared seventh wire rope, and the second pull rod and the fourth pull rod are connected with an elastic strip.

Preferably, when the first finger and the second finger are combined, the first arc rod and the inner arc of the second arc rod are arranged relatively, the first pull rod and the third pull rod are connected with the surgical robot power device through a shared fifth wire rope, and the second pull rod and the fourth pull rod are connected with the surgical robot power device through a shared sixth wire rope, so as to simplify the surgical robot power device.

Preferably, the first finger comprises a first arc rod, a first connecting pipe, a first joint shaft, a first pull rod, a second pull rod, an air bag and a sensor, wherein the air bag surrounds the first arc rod, a near end of the air bag is connected with a ventilation pipe, and the ventilation pipe is connected with an air pump of the surgical robot through an air path arranged on the mechanical arm, wherein the sensor comprises at least one or more of a pressure sensor, a blood pressure sensor, a heart rate sensor, a respiratory sensor, a blood oxygen saturation sensor, a temperature sensor, and a blood glucose sensor.

Preferably, the second finger comprises an air bag, the air bag surrounds the second arc rod or is arranged on one side of an inner arc of the second arc rod, a near end of the air bag is connected with a ventilation pipe, and the ventilation pipe is connected with an air pump of the surgical robot through an air path arranged on the mechanical arm.

Preferably, the air bag is also connected with an injection pump arranged on a body box of the surgical robot through the air path arranged on the mechanical arm.

Preferably, the air bag comprises a plurality of segments configured to increase a friction between the first finger and a fetus and enhance an effect of clamping and/or fixing the fetus.

Preferably, an inner arc surface of the air bag comprises a plurality of dense rough bumps configured to increase a friction between the first finger and the fetus, and enhance an effect of clamping and/or fixing the fetus.

Preferably, the wrist joint comprises a shell, a first anchorage, a second anchorage, an eighth steel wire rope, and a ninth steel wire rope. The shell is a spherical hollow shell structure, which includes a plurality of through holes configured to install fixed components or arranging transmission components. The first anchorage is arranged on an upper side of a far end of the shell. A far end of the eighth steel wire rope is fixedly connected with the first anchorage bypassing an outer surface of the shell, and connected with a power device of the surgical robot through transmission passing through holes of the first flange. The second anchorage is set at a lower side of a far end of the shell. A far end of a ninth wire rope is fixedly connected with the second anchorage, bypassing an external surface of the shell, and connected with a power unit of the surgical robot through transmission passing through the holes of the first flange so as to realize an extension and flexion of the wrist joint.

Preferably, the wrist joint comprises a shell, a first anchorage, an eighth steel wire rope, a second anchorage, and a ninth steel wire rope. The shell is a spherical hollow shell structure, which includes a plurality of through holes configured to install fixed components or arranging transmission components. The first anchorage is arranged on an upper side of a far end of the shell, a far end of the eighth steel wire rope is fixedly connected with the first anchorage, bypassing an outer surface of the shell, and connected with a power unit of the surgical robot through transmission passing through a plurality of holes of the first flange. The second anchorage is set at a lower side of the far end of the shell. A far end of the ninth wire rope is fixedly connected with the second anchorage, bypassing an external surface of the shell, and connected with a power unit of the surgical robot through transmission passing through the holes of the first flange, so as to realize an extension and flexion of the wrist joint.

Preferably, the wrist joint comprises a shell and a gyroscope, the gyroscope is arranged inside the shell configured to collect the wrist joint displacement data, thereby tracking and recording the fetus movement.

In one embodiment, the present invention provides a fetal intrauterine positioning and fixing mechanical arm, which comprises a host mechanical arm, a first auxiliary mechanical arm, and a second auxiliary mechanical arm. A far end of the host mechanical arm is connected with a manipulator, and a near end of the host mechanical arm is connected with the surgical robot or a handle, which is configured to assist the manipulator to enter an amniotic cavity, implement fetal positioning and fixing, and build an operation space for fetal intrauterine surgery.

Preferably, the host mechanical arm comprises an intra amniotic segment mechanical arm and an outer amniotic segment mechanical arm. A distal end of the intra amniotic segment mechanical arm is fixedly connected with s first flange, a proximal end of the intra amniotic segment mechanical arm is connected in series with the outer amniotic segment mechanical arm through a second flange, a distal end of the outer amniotic segment mechanical arm is connected in series with the intra amniotic segment mechanical arm through the second flange, and a proximal end of the outer amniotic segment mechanical arm is connected in series through a third flange and an adapter with a handle or the surgical robot.

Preferably, the intra amniotic segment mechanical arm comprises a first outer sleeve, an inner sleeve, a fourteenth wire rope, and a fifteenth wire rope. The first outer sleeve and the inner sleeve are made of flexible materials, so that the intra amniotic segment mechanical arm has a flexible performance. A distal end of the fourteenth wire rope is fixedly connected with an upper end of the first flange, a proximal end of the fourteenth wire rope is threaded through the first outer sleeve and the inner sleeve, and connected with a power unit of the surgical robot through transmission. The fifteenth wire rope is fixedly connected with a lower end of the first flange. A near end of the fifteenth wire rope passes through the first outer sleeve and the inner sleeve and connects with a power unit of the surgical robot through transmission.

Preferably, the intra amniotic segment mechanical arm is also partially penetrated into the outer amniotic segment mechanical arm, and the driving component of the outer amniotic segment mechanical arm can drive the intra amniotic segment mechanical arm to make rotary motion, and also drive the intra amniotic segment mechanical arm to make reciprocating motion.

Preferably, the intra amniotic segment mechanical arm is also divided into multiple segments, which is equivalent to adding at least one elbow joint to the intra amniotic segment mechanical arm, making the intra amniotic segment mechanical arm more attached to a maternal uterine wall, and helping to build a better surgical operation space.

Preferably, the outer amniotic segment mechanical arm comprises a second outer sleeve, a fixing rod and a driving component, wherein the second outer sleeve is configured to wrap and protect an inner structure of the outer amniotic segment mechanical arm, the fixing rod is connected with the second flange and the third flange to stabilize the structure of the outer amniotic segment mechanical arm, the driving component is electrically connected with the surgical robot, and drives the second flange to make the intra amniotic segment mechanical arm rotate.

Preferably, the first auxiliary mechanical arm uses a flexible mechanical arm or a rigid mechanical arm, including three or four degrees of freedom, including at least one degree of freedom of rotation. An end actuator of the first auxiliary mechanical arm is a suction cup, which is configured to cooperate with a main mechanical arm and the manipulator to implement fetus position adjustment.

Preferably, the suction cup comprises a disc body, a disc edge, a vent hole, a mounting joint, an air path and a sensor, wherein the disc body is a concave structure, a center of the concave structure is the vent hole, a periphery of the concave structure is the disc edge, the mounting joint is arranged on a convex side of the disc body to connect the first auxiliary mechanical arm, and the sensor is arranged on a concave side of the disc body to collect pressure data between the disc body and the fetus body, the vent hole is connected with an air pump of the surgical robot through the air path, and the air pump is electrically connected with a controller.

Preferably, the second auxiliary mechanical arm uses a flexible mechanical arm or a rigid mechanical arm. The second auxiliary mechanical arm includes three or four degrees of freedom, including at least one degree of freedom of rotation. The second auxiliary mechanical arm is configured to hold a camera, which can collect and transmit image signals, and provide image data for doctors when using the main mechanical arm, manipulator, and the first auxiliary mechanical arm to implement fetal positioning.

In one embodiment, the present invention provides a surgical robot for fetal intrauterine positioning and fixing, which includes an aforementioned mainframe mechanical arm and manipulator for fetal intrauterine positioning and fixing, a second auxiliary mechanical arm and a suction cup, a second auxiliary mechanical arm and a camera, and a surgical robot body.

Preferably, the surgical robot body comprises a power device, an air pump, an injection pump, a control processor, a drive device, a base, and a box. Using a master-slave operation mode, a doctor can remotely or near an operating table control the main mechanical arm and manipulator, the second auxiliary mechanical arm and suction cup, the second auxiliary mechanical arm and the camera to position and fix the fetus.

In one embodiment, the present invention provides a handle for fetal intrauterine positioning and fixing. The handle is connected with a main mechanical arm, a first auxiliary mechanical arm and a second auxiliary mechanical arm through transmission. A doctor can operate the main mechanical arm, the first auxiliary mechanical arm and the second auxiliary mechanical arm through the handle, which is used to transfer the main mechanical arm, the mechanical arm, the first auxiliary mechanical arm and a suction cup, the second auxiliary mechanical arm and a camera into an amniotic cavity through a vaginal cervical fetal membrane pathway or an abdominal wall uterine fetal membrane pathway to implement fetal positioning and body position fixation, and construct an operation space for fetal intrauterine surgery.

Preferably, the handle comprises a press switch, a holder, a control panel, a drive box and a connecting part, wherein the connecting part is configured to connect an outer amniotic segment mechanical arm and the handle, the drive box comprises a plurality of drive motors and a plurality of drive wire ropes, the drive motor is electrically connected with the control panel, the drive motor is powered by an external power supply, the drive wire rope is correspondingly connected with the main mechanical arm and a wire rope of the manipulator, the control panel adopts a touch screen and a plurality of human-machine interaction modes for a doctor to give instructions and control the driving motor, the main machine arm and the manipulator.

In one embodiment, the present invention provides a fetal intrauterine positioning and fixing system, which includes an operating system, a control system, and a positioning and navigation system.

Preferably, the control system includes an image processing module, a surgical planning module, a mechanical arm control module, and a fetal motion track module.

Preferably, the positioning and navigation system includes an imaging module, a tracking module and a display module. According to a plurality of preoperative imported images, a dynamic three-dimensional model is formed. The dynamic three-dimensional model is unified with an actual body position of a fetus and a mother, and a real-time position of a manipulator and a suction cup in the same coordinate system in a space. By observing a corresponding position relationship between the manipulator, the suction cup sucker and a lesion in the dynamic three-dimensional model, a doctor can adjust and fixe the fetus position to build a surgical treatment space.

In one embodiment, the present invention provides an intrauterine fetal positioning and fixing method, which is used for a one-bore surgical robot scheme of entering an amniotic cavity through a vagina, cervix and fetal membrane to adjust and fix a fetal position, and construct a surgical treatment space. The method includes a plurality of steps as follows.

S110, plan a fetal intrauterine positioning and fixing path;

S120, create a passage through a vagina, cervix and fetal membrane into an amniotic cavity;

S130, insert a second auxiliary mechanical arm and a camera;

S140, insert a first auxiliary mechanical arm and a suction cup;

S150, insert a main machine arm and a manipulator;

S160, position a fetus;

S170, withdraw the first auxiliary machine arm and the suction cup, then fix the fetus;

S180, dynamic adjust fetal position during operation;

S190, after the operation, release the fetus by the main machine arm and manipulator and withdraw.

Further, in step S120, the one-bore surgical robot scheme of entering an amniotic cavity can be performed through an abdominal wall uterine fetal membrane to adjust and fix the fetal position, build a surgical treatment space, and implement surgical treatment.

Preferably, a two-bore surgical robot scheme of entering an amniotic cavity can be performed through both a vaginal cervix fetal membrane and an abdominal wall uterine fetal membrane to adjust and fix the position of the fetus and build a surgical treatment space, which includes a plurality of steps as follow.

S210, plan a fetal intrauterine positioning and fixing path;

S220, create a passage through both the vaginal cervix fetal membrane and the abdominal wall uterine fetal membrane into an amniotic cavity;

S230, insert a second auxiliary mechanical arm and a camera, a first auxiliary mechanical arm and a suction cup, and a main machine arm and a manipulator as in step 130, step 140 and step 150;

S240, position a fetus, withdraw the first auxiliary machine arm and the suction cup, then fix the fetus, and dynamic adjust fetal position during operation;

S250, after the operation, release the fetus by the main machine arm and manipulator and withdraw.

Beneficial Effect (1) Accurately adjustment body position. A surgical robot or a doctor controls a mechanical arm and manipulator to enter the amniotic cavity through a natural cavity of the vagina and cervix or through an abdominal small wound. According to a preoperative planning, with the help of the mechanical arm holding a fetus body or limb and/or a suction cup adsorbing the fetus body or limb, pushing, pulling or dragging can be implemented to adjust the body position of the fetus in uterus, so that a part or area that the fetus is scheduled to receive surgical treatment is close to a surgical approach, such as an internal opening of cervix or abdominal wound.

(2) Accurately fixation the fetus body position and build a surgical space. After the surgical robot or the doctor controls the main machine arm and manipulator to adjust the fetal position in place, the manipulator can hold the fetal body or limb, fine tune the fetal position, fully expose the surgical treatment area, and withdraw the first auxiliary manipulator. An intra amniotic segment of the main machine arm can be close to the uterine wall, so as to build an operating space for safe and accurate intrauterine fetal surgery.

(3) Real time fetal physiological monitoring. The sensors of the manipulator collect the fetus blood pressure, heart rate, respiration, blood oxygen saturation, temperature and other data in real time to provide the doctor with a real-time information about the fetal status during the operation.

(4) The air bag prevents the fetus from being crushed. The arc rods of the first and second finger can carry the air bags with a diameter of no more than 1 mm, and pass through a small natural cavity or wound. The arc rods can have a diameter of more than 10 mm after the air bag inflates. When the fetus body or limb is clamped for a long time, crushing damage can be avoided. In addition, combined with the data collected by the pressure sensor, the pressure exerted on the fetal body by the manipulator can be controlled in an appropriate range to further avoid crushing and damaging the fetus.

(5) The fetal position can be adjusted immediately during operation. Special mechanical arms and manipulator are used for fetal positioning and fixation, which can be adjusted in real time according to the needs of the doctor. For example, when the operating mechanical arm encounters a blind area and changes the surgical site, the fetal position can be adjusted in real time, thus shortening the operation time.

(6) In addition to adapting to the surgical robot, the mechanical arm and manipulator can also adapt to a handle. Combined with conventional laparoscopic technology, intrauterine fetal surgery can be carried out to increase application scenarios.

These and other objectives, features, and advantages of the present invention will become apparent from the following detailed description, the accompanying drawings, and the appended claims.

BRIEF DESCRIPTION OF THE DRAWINGS

In order to more clearly explain the technical solution of the embodiments of the present invention, the following briefly introduces the drawings needed to be used in the description of the embodiments. Obviously, the drawings in the following description are only some embodiments of the present invention. For those skilled in the art, other drawings can be obtained from these drawings without any creative effort.

In addition, the drawings are only schematic diagrams of the invention and are not necessarily drawn to scale. The same reference numerals in the figures represent the same or similar parts, and therefore repeated description of them will be omitted. Some block diagrams shown in the figures are functional entities, which do not necessarily correspond to physically or logically independent entities. These functional entities can be implemented in one or more hardware modules or component combinations.

FIG. 33 is a flow chart of fetal intrauterine positioning and fixation according to the embodiment of the present invention.

Figure 1:
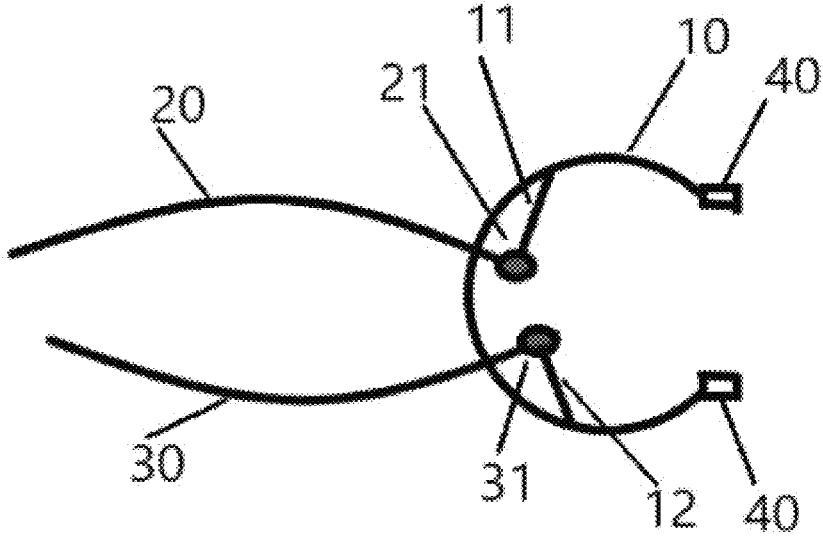
FIG. 1 is a structural diagram of a manipulator including a wrist joint, a first finger and a second finger according to a preferred embodiment of the present invention.

The drawings, described above, are provided for purposes of illustration, and not of limitation, of the aspects and features of various examples of embodiments of the invention described herein. The drawings are not intended to limit the scope of the claimed invention in any aspect. For simplicity and clarity of illustration, elements shown in the drawings have not necessarily been drawn to scale and the dimensions of some of the elements may be exaggerated relative to other elements for clarity.

DETAILED DESCRIPTION OF THE PREFERRED EMBODIMENT

In order to make the purpose, technical solution and advantages of the present invention more clearly, the present invention is further described in detail below in combination with embodiments. It should be understood that the preferred embodiments described herein are only used to explain the present invention, not to limit the present invention.

It should be noted that the upper, lower, left, right, far, near, front and rear directions in the embodiment are only relative concepts to each other or refer to the normal use state of the product, and should not be considered as restrictive.

Referring to FIGS. 1 to 22, an intrauterine positioning manipulator according to a preferred embodiment of the present invention can enter an amniotic cavity through a vaginal cervix or abdominal wound, identify and adjust a fetus position, fix the fetus, and monitor the fetus status in real time with a help of a surgical robot or a doctor.

As shown in FIG. 1, a fetal intrauterine positioning manipulator according to the embodiment of the present invention can comprises a wrist joint 10, a first finger 20 and a second finger 30. A proximal end of the wrist joint 10 can be connected with a power device of a surgical robot through a first flange 40. The proximal end of the wrist joint 10 can be connected with the first flange 40 in a sliding connection. The proximal end of the wrist joint 10 can rotate in a sliding way under a restriction of the first flange 40. A distal end of the wrist joint 10 can be fixedly connected with a first finger wrist joint axis 21 of the first finger 20 through a first connecting column 11, and the distal end of the wrist joint 10 can also be fixedly connected with a second finger wrist joint 31 of the second finger 30 through a second connecting column 12. The first finger wrist joint 21 is equivalent to a joint axis between the first finger 20 and the wrist joint 10, and the second finger wrist joint 31 is equivalent to a joint axis between the second finger 30 and the wrist joint 10. The first finger 20 and the second finger 30 can cooperate with each other to implement an opening and closing action under a driving of the power device of the surgical robot. Driven by the wrist joint 10, the first finger 20 and the second finger 30 can perform up and down flexion and extension, left and right swing and rotation movements, so as to complete a clamping, releasing, pulling, dragging, and fixed braking of a fetus trunk and/or limb.

It can be understood that the fetal intrauterine positioning manipulator can include the wrist joint 10, the first finger 20, the second finger 30, and more than two fingers for more complex grip adjustment and fixation of the fetus trunk and/or limbs. The fetal intrauterine positioning manipulator can also include the wrist joint 10 and the first finger 20. The first finger 20 includes a plurality of interphalangeal joints, which can be long enough to hold and adjust the fetus trunk and/or limbs, so that the first finger 20 can replace a function of two or more fingers. Of course, the fetal intrauterine positioning manipulator can also include only the first finger 20. The first finger 20 includes multiple interphalangeal joints, of which at least one interphalangeal joint has a rotation function. The first finger 20 is long enough to hold and adjust the fetal trunk or limbs, like an elephant trunk, so that the intrauterine fetus can be positioned and fixed.

Figure 2:
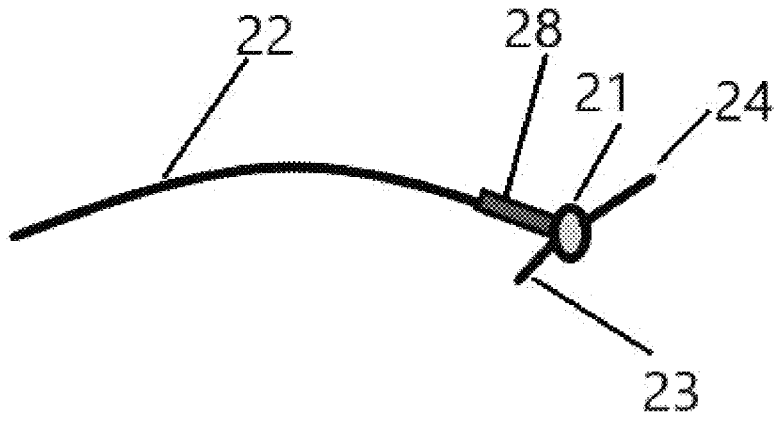
FIG. 2 is a schematic diagram of the first finger structure described in FIG. 1 according to the embodiment of the present invention.

As shown in FIG. 2, the first finger 20 of a fetal intrauterine positioning manipulator in the embodiment of the present invention can include a first arc rod 22, a first connecting tube 28, a first finger-wrist joint 21, a first pull rod 23, and a second pull rod 24. The first arc rod 22 can be detachably connected with the first connecting tube 28. The first connecting tube 28, the first pull rod 23, and the second pull rod 24 can rotate around the first finger-wrist joint 21, and the first connecting tube 28, the first pull rod 23 and the second pull rod 24 can be fixedly connected with each other.

It should be noted that an inner arc of the first arc rod 22 can be a side that is expected to contact the fetus. A radian and length of the first arc rod 22 can be designed as a series of products, or even can be 3D printed to meet a need. The first arc rod 22 usually adopts elastic stiffness memory material, which is conducive to deformation through a narrow space. A rod body diameter of the first arc rod 22, the first connecting pipe 28, the first pull rod 23 and the second pull rod 24 usually does not exceed 1 mm.

Figure 3:
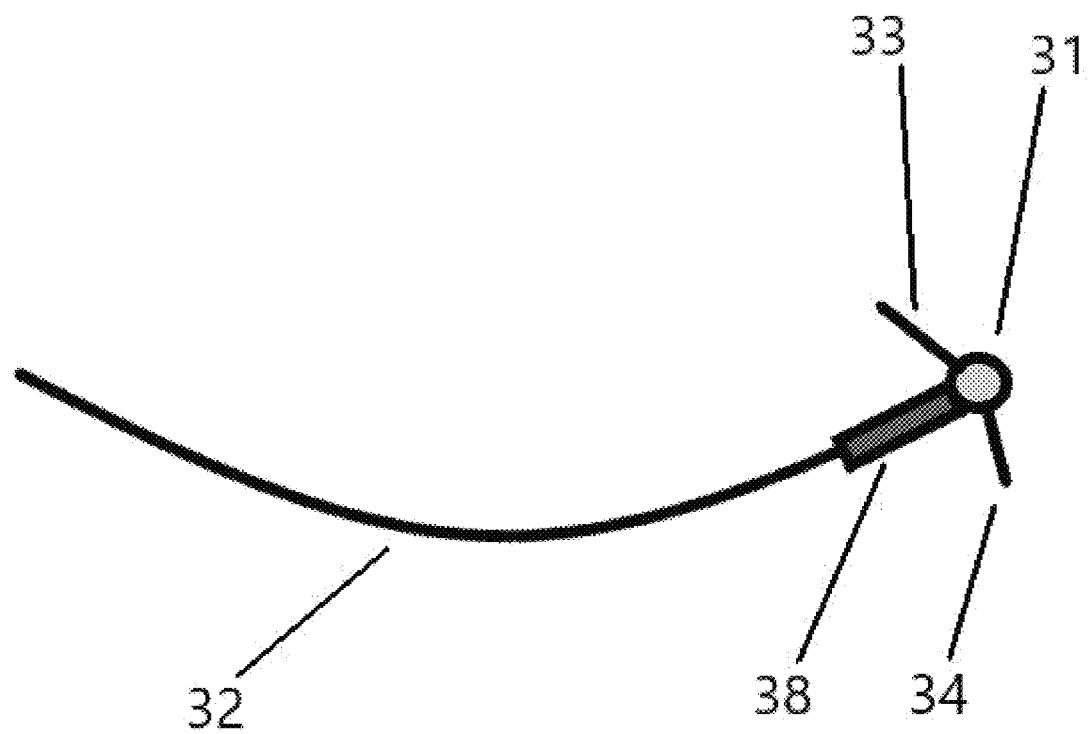
FIG. 3 is a schematic diagram of the second finger structure described in FIG. 1 according to the embodiment of the present invention.

As shown in FIG. 3, the second finger 30 of a fetal intrauterine positioning manipulator according to the embodiment of the present invention can comprises a second arc rod 32, a second connecting tube 38, a second finger-wrist joint 31, a third pull rod 33, and a fourth pull rod 34. The second arc rod 32 can be detachably connected with the second connecting tube 38. The second connecting tube 38, the third pull rod 33, and the fourth pull rod 34 can rotate around the second finger-wrist joint 31, and the second connecting tube 38, the third pull rod 33 and the fourth pull rod 34 can be fixedly connected with each other.

It should be noted that an inner arc of the second arc rod 32 can be a side that is expected to contact the fetus. A radian and length of the second arc rod 32 can be designed as a series of products, or even can be 3D printed to meet a need. The second arc rod 32 usually adopts elastic stiffness memory material, which is conducive to deformation through a narrow space. A rod body diameter of the second arc rod 32, the second connecting pipe 38, the third pull rod 33 and the fourth pull rod 34 usually does not exceed 1 mm.

Figure 4:
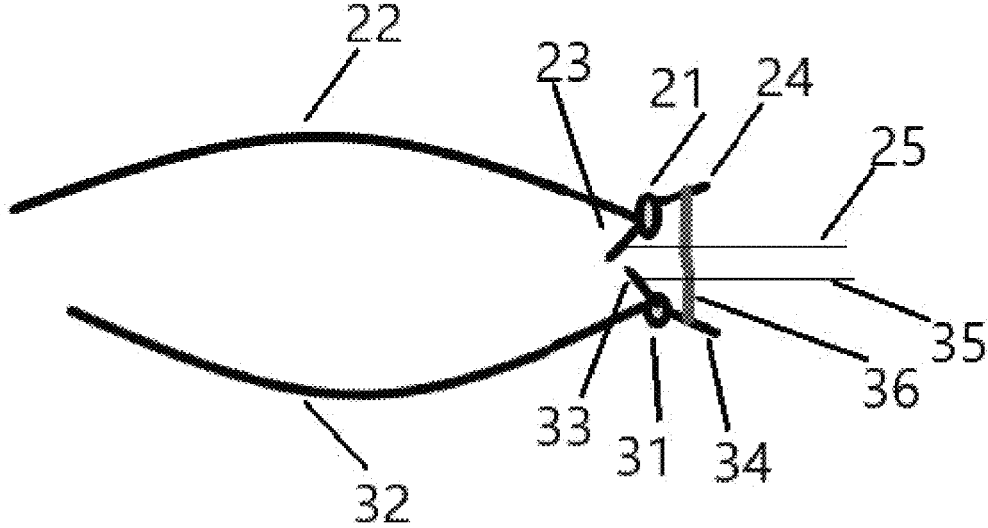
FIG. 4 is a schematic diagram of a combination structure of the first finger and the second finger of the embodiment of the present invention, as described in FIGS. 2 and 3.

As shown in FIG. 4, a combination connection of the first finger 20 and the second finger 30 can be configured to clamp and/or hold the fetus body or limb according to the embodiment of the present invention. The first arc rod 22 and the inner arc of the second arc rod 32 can be arranged in a relative manner. The first pull rod 23 can be connected with the power device of the surgical robot through a first steel wire rope 25, the third pull rod 33 can be connected with the power device of the surgical robot through a second steel wire rope 35 in a transmission connection manner, and there is an elastic strip 36 between the second pull rod 24 and the fourth pull rod 34. A rebound force provided by the elastic strip 36 can shorten a distance between the second pull rod 24 and the fourth pull rod 34. Accordingly, a distance between the first arc rod 22 and the second arc rod 32 can increase to form an opening for incorporation into the fetus trunk and/or limb. When a power unit of the surgical robot is started, the first wire rope 25 and the second wire rope 35 respectively pull the first pull rod 23 and the third pull rod 33, which can reduce a distance between the first arc rod 22 and the second arc rod 32 configured to clamp or fix the fetus trunk or limbs.

It should be noted that the elastic strip 36 can be a rubber strip or a spring, and its resilience can be customized according to needs. A traction force provided by the power device of the surgical robot for the first wire rope 25 and the second wire rope 35 is limited to a certain range to ensure that the first arc rod 22 and the second arc rod 32 do not damage the fetus when clamping or fixing the fetus trunk and/or limbs.

Figure 5:
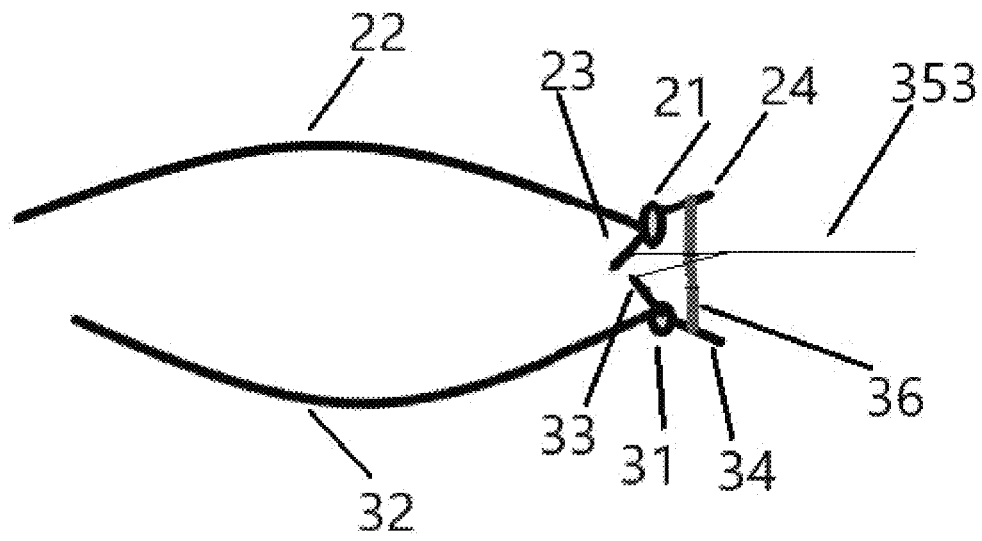
FIG. 5 is the second schematic diagram of a combination structure of the first finger and the second finger according to the embodiment of the present invention, as described in FIGS. 2 and 3.

In addition, as shown in FIG. 5, the first finger 20 and the second finger 30 in the embodiment of the present invention can be combined to clamp and/or hold the fetus body and/or limb. The first arc rod 22 and an inner arc of the second arc rod 32 are arranged in a relative manner. The first pull rod 23 and the third pull rod 33 can be connected with the power device of the surgical robot through a shared seventh wire rope 353. The elastic strip 36 can be arranged between the second pull rod 24 and the fourth pull rod 34. The rebound force provided by the elastic strip 36 can shorten the distance between the second pull rod 24 and the fourth pull rod 34. Accordingly, the distance between the first arc rod 22 and the second arc rod 32 can increase to form an opening for incorporation into the fetus trunk or limb. When the power device of the surgical robot is started, the seventh wire rope 353 can pull the first pull rod 23 and the third pull rod 33, which can reduce the distance between the first arc rod 22 and the second arc rod 32 configured to clamp or fix the fetus trunk or limb.

Figure 6:
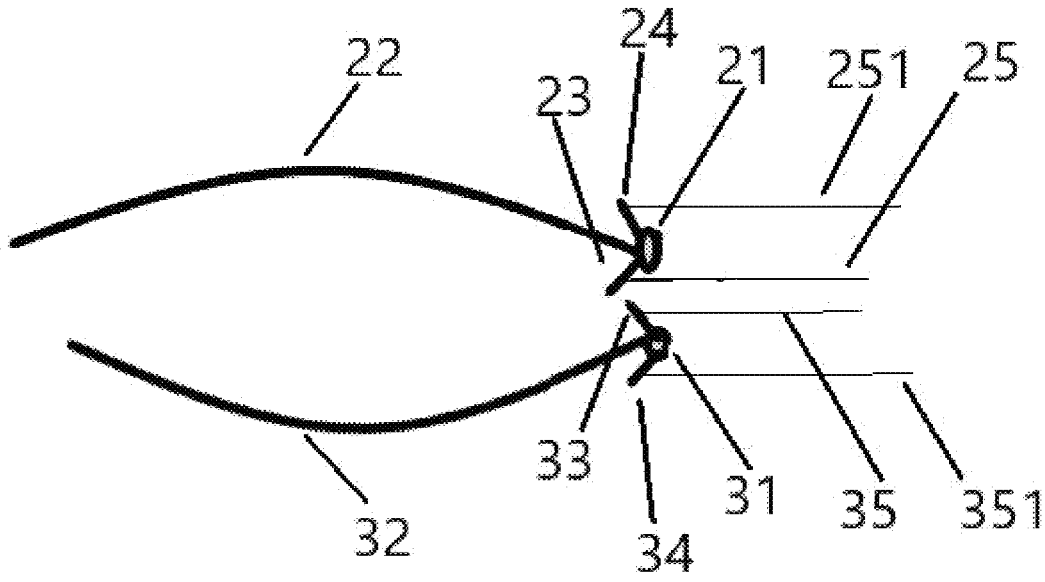
FIG. 6 is the third schematic diagram of a combination structure of the first finger and the second finger according to the embodiment of the present invention, as described in FIGS. 2 and 3.

As shown in FIG. 6, the first finger 20 and the second finger 30 in the embodiment of the present invention can also be combined to clamp and/or hold the fetus body and/or limb. The first arc rod 22 and the inner arc of the second arc rod 32 can be arranged in a relative manner. The first pull rod 23 can be connected with the power device of the surgical robot through the first wire rope 25, the second pull rod 24 can be connected with the power device of the surgical robot through a third wire rope 251, the third pull rod 33 can be connected with the power device of the surgical robot through the second wire rope 35, and the fourth pull rod 34 can be connected with the power device of the surgical robot through the fourth wire rope 351 in a transmission connection manner respectively. When the power device of the surgical robot is started, and the first wire rope 25 and the second wire rope 35 respectively pull the first pull rod 23 and the third pull rod 33, which can reduce the distance between the first arc rod 22 and the second arc rod 32 so as to clamp or fix the fetus trunk or limbs. When the power unit of the surgical robot is started, the third wire rope 251 and the fourth wire rope 351 pull the second pull rod 24 and the fourth pull rod 34 respectively, so that the first arc rod 22 and the second arc rod 32 can be separated from each other to accommodate the fetus trunk or limb.

It should be noted that the power device of the surgical robot can include a plurality of independent power drive units which can be connected with a plurality of different wire ropes.

In addition, as shown in FIG. 6, the first finger 20 and the second finger 30 can be combined and connected, a plurality of independent power drive units of the surgical robot can start at the same time and drive a plurality of different wire ropes at the same time. According to a system command, under a control of the surgical robot control processor, a driving force exerted by each independent power drive units on each different wire ropes can be accurately controlled, then the first pull rod 23, the second pull rod 24, the third pull rod 33 and the fourth pull rod 34 can accurately control the distance between the first arc rod 22 and the second arc rod 32, which is configured to accurately control a precise clamping and/or release of the fetus trunk and/or limb.

Figure 7:
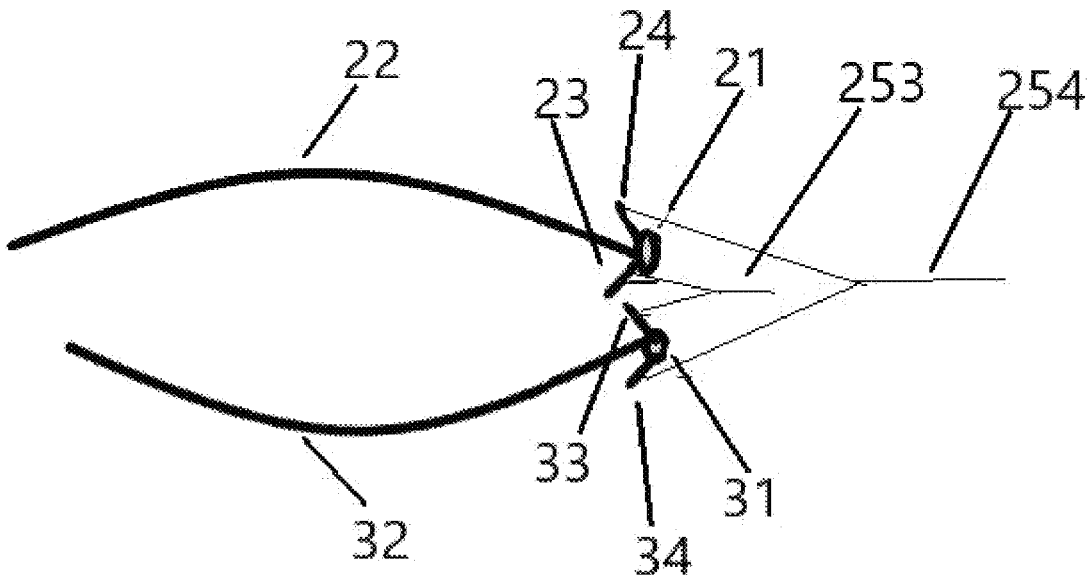
FIG. 7 is the fourth schematic diagram of a combination structure of the first finger and the second finger according to the embodiment of the present invention, as described in FIGS. 2 and 3.

In addition, as shown in FIG. 7, the first finger 20 and the second finger 30 in the embodiment of the present invention can be combined to clamp and/or hold the fetus body and/or limb. The first arc rod 22 can be arranged relative to an inner arc of the second arc rod 32. The first pull rod 23 and the third pull rod 33 are connected with the surgical robot power device through a shared fifth wire rope 253 in a transmission connection. The second pull rod 24 and the fourth pull rod 34 are connected with the surgical robot power device through a shared sixth wire rope 254, which can reduce a number of independent power drive units of the surgical robot power device, thus, the device can be simplified. When the power units of the surgical robot is started, the fifth wire rope 253 can pull the first pull rod 23 and the third pull rod 33, which can reduce the distance between the first arc rod 22 and the second arc rod 32 so as to clamp or fix the fetus trunk and/or limb. When the power device of the surgical robot is started, the sixth wire rope 254 can pull the second pull rod 24 and the fourth pull rod 34, so that the first arc rod 22 and the second arc rod 32 can be separated from each other to accommodate the fetus trunk and/or limb.

Figure 8:
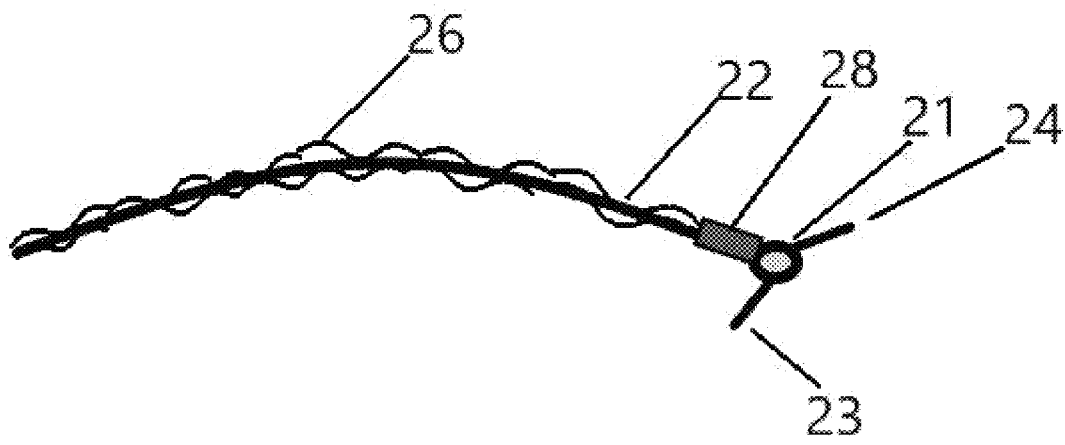
FIG. 8 is a structural diagram of the first finger as described in FIG. 1 including an uninflated airbag according to the embodiment of the present invention.
Figure 9:
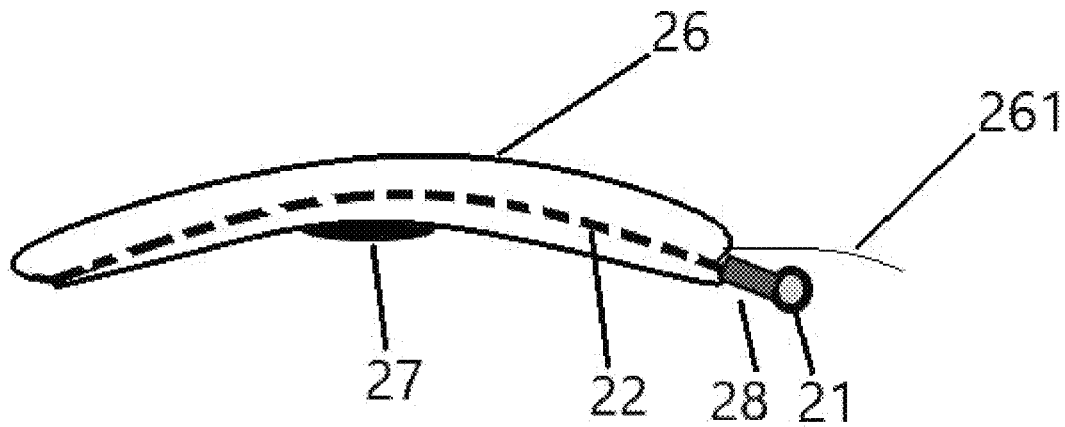
FIG. 9 is a structural diagram of the first finger as described in FIG. 1 including an inflated airbag according to the embodiment of the present invention.

As shown in FIGS. 8 and 9, according to the embodiment of the present invention the first finger 20 can comprise a first arc rod 22, a first connecting tube 28, a first joint shaft 21, a first pull rod 23, a second pull rod 24, an air bag 26, and a plurality of sensors 27. The air bag 26 surrounds the first arc rod 22, a near end of the air bag 26 can connect with a vent pipe 2261, and the vent pipe 2261 can be connected with an air pump of the surgical robot through an air path arranged on a mechanical arm. Generally, the air bag 26 is not inflated, the air bag wall is attached to the first arc rod 22, and a wall thickness of the air bag 26 is usually not more than 0.1 mm, which is conducive to the first finger 20 entering an amniotic cavity through a narrow channel. When the air bag 26 is inflated, the air bag 26 is cylindrically, a diameter of the air bag 26 can exceed 10 mm. Among them, the sensors 27 can use a flexible circuit chip, which is electrically connected to the surgical robot and arranged along an inner arc axis of the air bag 26 to ensure close contact with a fetus body. The sensors 27 can accurately collect fetal physiological data. The sensors 27 can comprise a pressure sensor, a blood pressure sensor, a heart rate sensor, a respiration sensor, a blood oxygen saturation sensor, a temperature sensor, a blood glucose sensor.

In addition, the airbag 26 can also be connected with an injection pump set on a body box of the surgical robot through the air path set on a mechanical arm to fill the air bag 26 with liquid as required, such as normal saline and artificial amniotic fluid, so as to prevent a buoyancy of the airbag 26 after inflation from affecting a stability of positioning operation and fixed fetal position.

Figure 10:
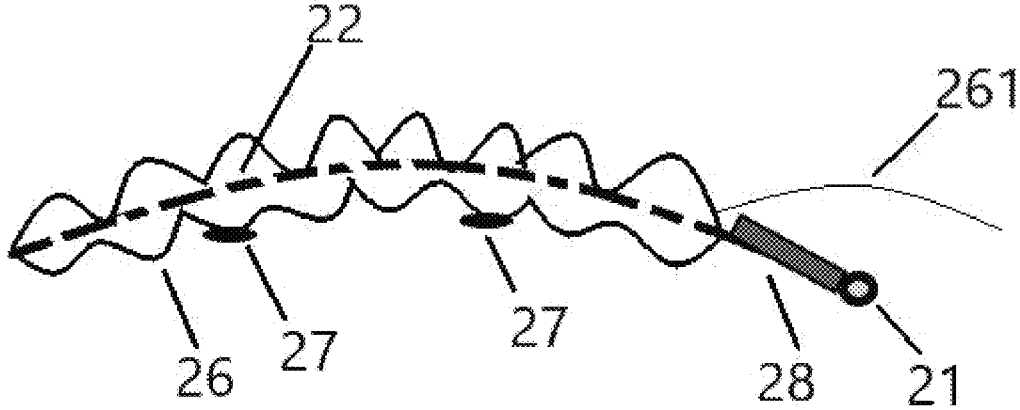
FIG. 10 is a structural diagram of the first finger as described in FIG. 1 including a segmented inflatable airbag according to the embodiment of the present invention.

In addition, as shown in FIG. 10, the air bag 26 can be divided into a plurality of segments to increase a friction between the first finger 20 and the fetus body when the first finger 20 clamps or fixes the fetus trunk and/or limb, so as to enhance an effect of clamping and/or fixing the fetus. Accordingly, the sensors 27 can be arranged at a highest point of a bulge of an inner arc axis of the air bag 26, so as to achieve the effect that the sensors 27 closely contact the fetus body.

Figure 16:
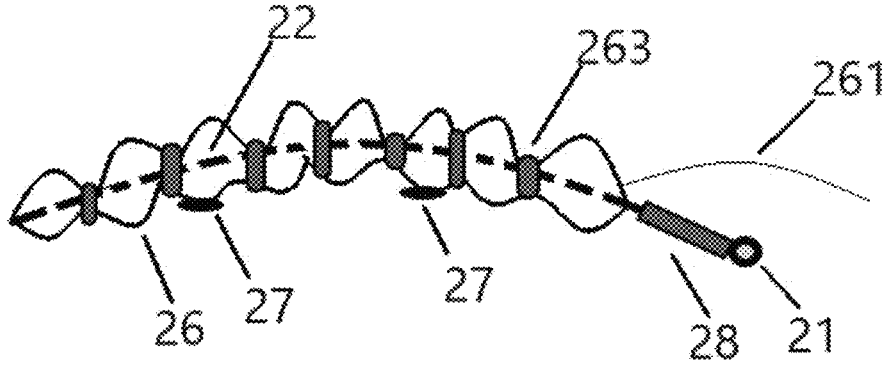
FIG. 16 is another structural diagram of the first finger as described in FIG. 1 including a segmented inflatable airbag and a plurality of fixed bundles according to the embodiment of the present invention.

Further, as shown in FIG. 16, a plurality of binding bands 263 can be set between the segments of the air bag 26, and the binding bands 263 can accurately control a shape of each segment of the air bag 26, so as to achieve a stable and enhanced fetus clamping and/or fixation effect.

Figure 14:
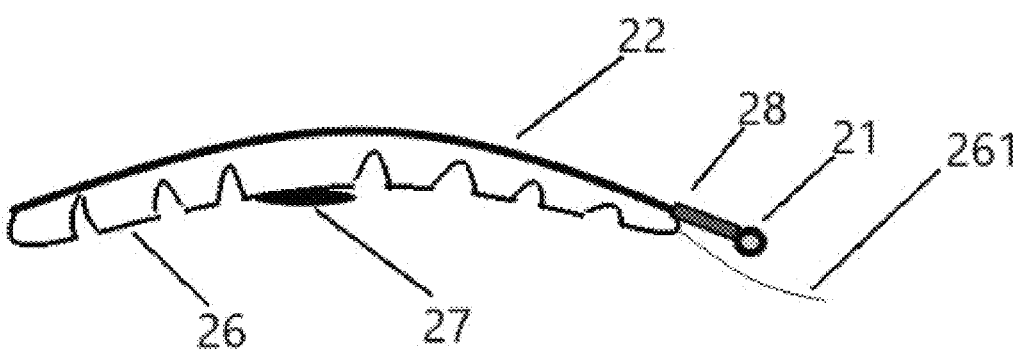
FIG. 14 is another structural diagram of the first finger as described in FIG. 1 including a segmented inflatable airbag according to the embodiment of the present invention.

Further, as shown in FIG. 14, a plurality of dense rough bumps (not shown) can be set on an inner arc surface of the air bag 26 so as to increase a friction between the first finger 20 and the fetus body and enhance an effect of clamping and/or fixing the fetus.

Accordingly, the second finger 30 can adopt a same air bag 26 structure as the first finger 20, and the first finger 20 and the second finger 30 can cooperate with each other to enhance an effect of clamping and/or fixing the fetus.

Figure 15:
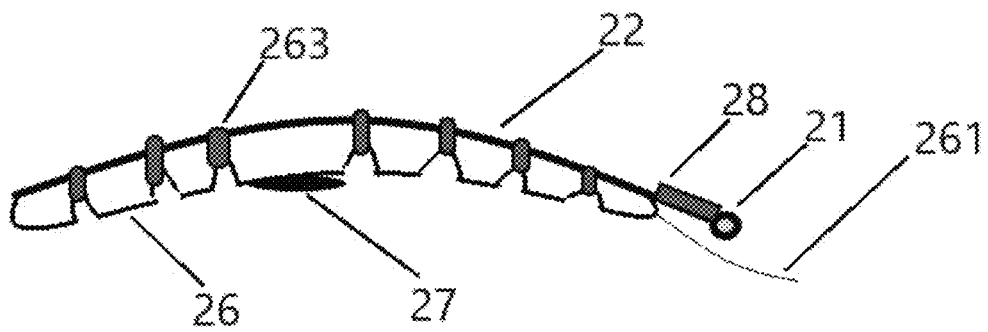
FIG. 15 is a structural diagram of the first finger as described in FIG. 1 including a segmented inflatable airbag and a plurality of fixed bundles according to the embodiment of the present invention.

As shown in FIGS. 15 and 16, according to the embodiment of the present invention the first finger 20 can comprise a first arc rod 22, a first connecting tube 28, a first wrist joint shaft 21, a first rod 23, a second rod 24, an air bag 26, and a plurality of sensors 27. The air bag 26 is arranged on an inner arc side of the first arc rod 22, a near end of the air bag 26 is connected with a vent pipe 2261, and the vent pipe 2261 is connected with to air pump of a surgical robot through an air path arranged on a mechanical arm. Generally, the air bag 26 is in an uninflated state, a wall of the air bag 26 is attached to the first arc rod 22, with a thickness no more than 0.1 mm, which is conducive to the first finger 20 entering an amniotic cavity through a narrow channel. When the air bag 26 is inflated, the air bag 26 is cylindrical and located at the inner arc side of the first arc rod 22, while the diameter of the air bag 26 may exceed 10 mm. The sensors 27 can adopt a flexible circuit chip, which is electrically connected with a surgical robot and arranged along an inner arc axis of the air bag 26. The sensors 27 can include at least one or more combinations of a pressure sensor, a blood pressure sensor, a heart rate sensor, a respiratory sensor, a blood oxygen saturation sensor, a temperature sensor and a blood glucose sensor. In addition, the air bag 26 can also be connected with an injection pump set on the surgical robot through an air path set on a mechanical arm to fill the air bag 26 with liquid as required, such as normal saline and/or artificial amniotic fluid, so as to avoid a buoyancy of the air bag 26 after inflation affecting a stability of positioning operation and fetal position fixation.

In addition, as shown in FIG. 14, the air bag 26 can be divided into a plurality of segments to increase a friction between the first finger 20 and the fetus body when the first finger 20 clamps and/or fixes the fetus trunk and/or limb, so as to enhance an effect of clamping and/or fixing the fetus. Accordingly, the sensors 27 can be arranged at a highest point of a bulge of an inner arc axis of the segment of the air bag 26, so as to achieve an effect that the sensors 27 can closely contact the fetus body.

Further, as shown in FIG. 15, a plurality of binding bands 263 can be set between a plurality of segments of the air bag 26, and the binding bands 263 can accurately control a shape of each segment of the air bag 26, so as to achieve a stable and enhanced fetal clamping and/or fixation effect.

Figure 11:
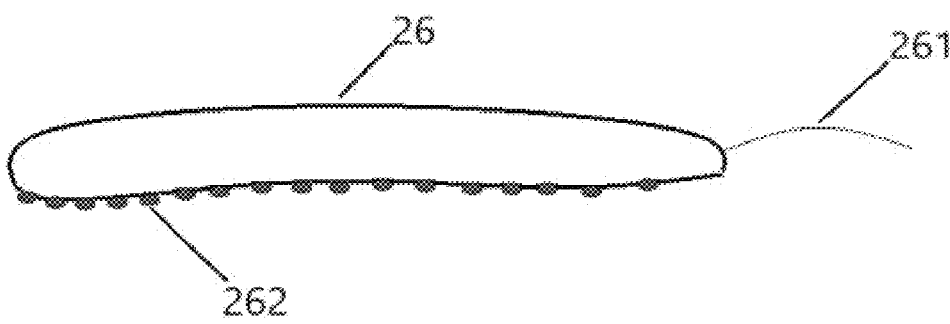
FIG. 11 is a structural diagram of an air bag with a plurality of rough bumps according to the embodiment of the present invention.
Figure 12:
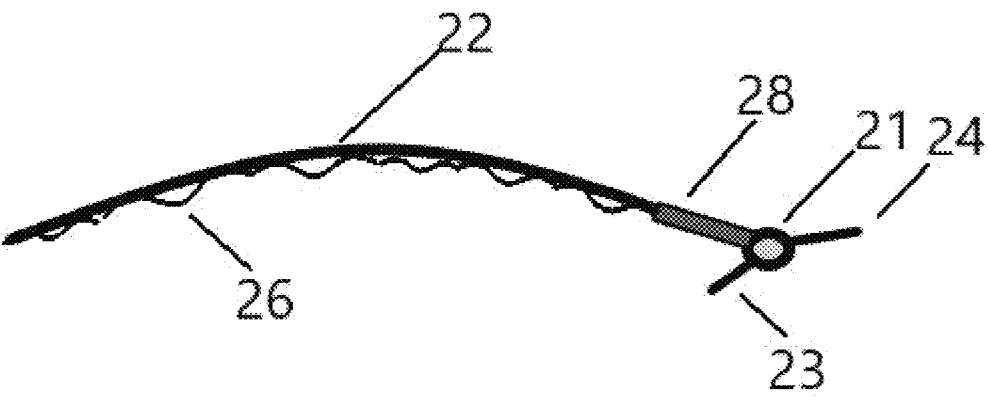
FIG. 12 is another structural diagram of the first finger as described in FIG. 1 including an uninflated airbag according to the embodiment of the present invention.
Figure 13:
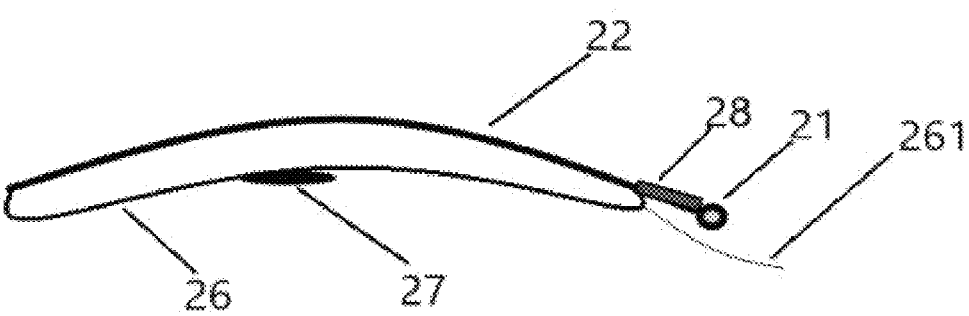
FIG. 13 is another structural diagram of the first finger as described in FIG. 1 including an inflated airbag according to the embodiment of the present invention.

Further, as shown in FIG. 11, a plurality of dense rough bumps (not shown) can be set on an inner arc surface of the air bag 26 to increase a friction between the first finger 20 and the fetus body and enhance an effect of clamping and/or fixing the fetus.

Accordingly, the second finger 30 can adopt a same air bag 26 structure as the first finger 20, and the first finger 20 and the second finger 30 can cooperate with each other to enhance an effect of clamping and/or fixing the fetus.

Referring to FIGS. 1 and 17 to 22, according to the embodiment of the present invention a proximal end of the wrist joint 10 of a fetal intrauterine positioning manipulator can be connected with a power device of the surgical robot through a first flange 40, the proximal end of the wrist joint 10 can be connected with the first flange 40 in a sliding way, and the proximal end of the wrist joint 10 can rotate in a sliding way under a restriction of the first flange 40.

Figure 17:
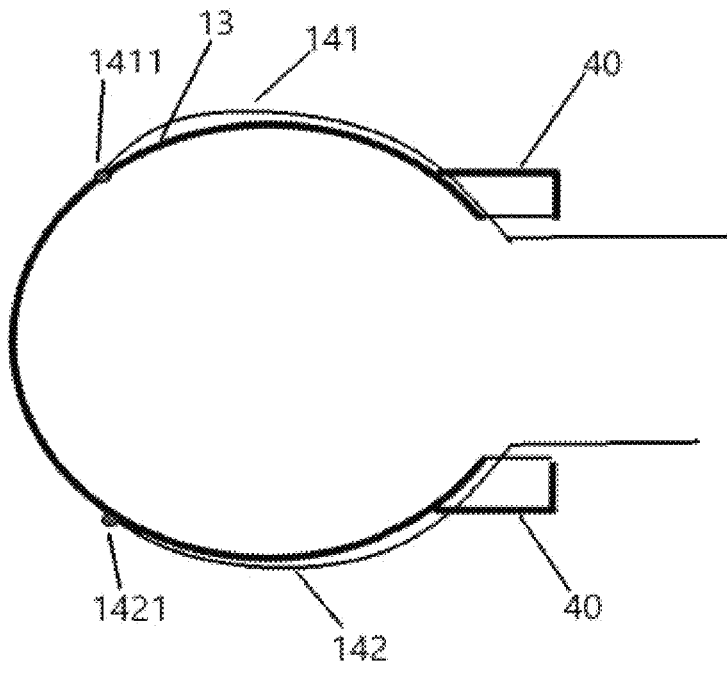
FIG. 17 is a schematic diagram of a first wrist joint transmission connection structure according to the embodiment of the present invention.

As shown in FIG. 17, according to the embodiment of the present invention a main structure of a wrist joint 10 can comprise a shell 13, a first anchorage 1411, an eighth steel wire rope 141, a second anchorage 1421, and a ninth steel wire rope 142. The shell 13 can be a spherical hollow shell structure, and the spherical hollow shell structure is provided with a plurality of holes configured to install fixed components and/or arranging transmission components. Wherein, the first anchorage 1411 can be arranged on an upper side of a far end of the shell 13, a far end of the eighth steel wire rope 141 can be fixedly connected with the first anchorage 1411, bypassing an outer surface of the shell 13, passing through a hole of a first flange 40 to be connected with a power device of a surgical robot, the second anchorage 1421 can be arranged on a lower side of a far end of the shell 13, a far end of the ninth steel wire rope 142 can be fixedly connected with the second anchorage 1421, bypassing an outer surface of the shell 13, through the hole of the first flange 40 and the power device of the surgical robot. When the power device of the surgical robot starts to pull the eighth wire rope 141, loosen the ninth wire rope 142, and the shell 13 turns upward relying on the first flange 40, a wrist flexion motion of the wrist joint 10 will be realized. When the power device of the surgical robot starts to pull the ninth wire rope 142, loosen the eighth wire rope 141, the shell 13 turns down on the first flange 40 to achieve a wrist extension of the wrist joint 10.

It should be noted that a position of the first anchorage 1411 or the second anchorage 1421 set at the far end of the shell 13 can generally be close to a far end vertex of the shell 13 of the spherical hollow shell structure, and a degree of flexion and extension of the wrist joint 10 can reach or exceed 90 degrees.

Figure 18:
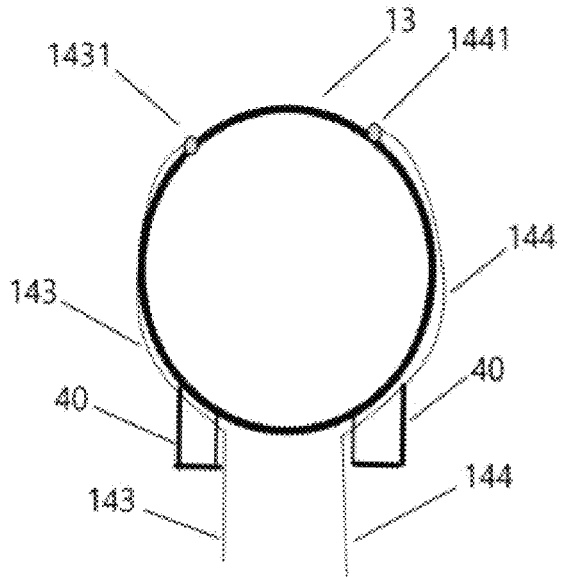
FIG. 18 is a schematic diagram of a second wrist joint transmission connection structure according to the embodiment of the present invention.

In addition, as shown in FIG. 18, according to the embodiment of the present invention a main structure of a wrist joint 10 can comprise a main structure of a wrist joint 10 can comprise a shell 13, a third anchorage 1431, a tenth steel wire rope 143, a fourth anchorage 1441, and an eleventh steel wire rope 144. The shell 13 can be a spherical hollow shell structure, and the spherical hollow shell structure can be provided with a plurality of holes for installing fixed components or arranging transmission components. Wherein, the third anchorage 1431 can be arranged on a left side of a far end of the shell 13, a far end of the tenth steel wire rope 143 can be fixedly connected with the third anchorage 1431, bypassing an outer surface of the shell 13, passing through a hole of a first flange 40 and being connected with a power device of a surgical robot, the fourth anchorage 1441 can be arranged on a right side of a far end of the shell 13, a far end of the eleventh steel wire rope 144 can be fixedly connected with the fourth anchorage 1441, bypassing an outer surface of the shell 13, through the hole of the first flange 40 and the power device of the surgical robot. When the power device of the surgical robot starts to pull the tenth wire rope 143, loosen the eleventh wire rope 144, and the shell 13 turns to a left relying on the first flange 40, a left wrist flexion motion of the wrist joint 10 can be achieved. When the power device of the surgical robot starts to pull the eleventh wire rope 144, loosen the tenth wire rope 143, the shell 13 turns to a right by relying on the first flange 40 to realize a right wrist extension of the wrist joint 10.

Figure 19:
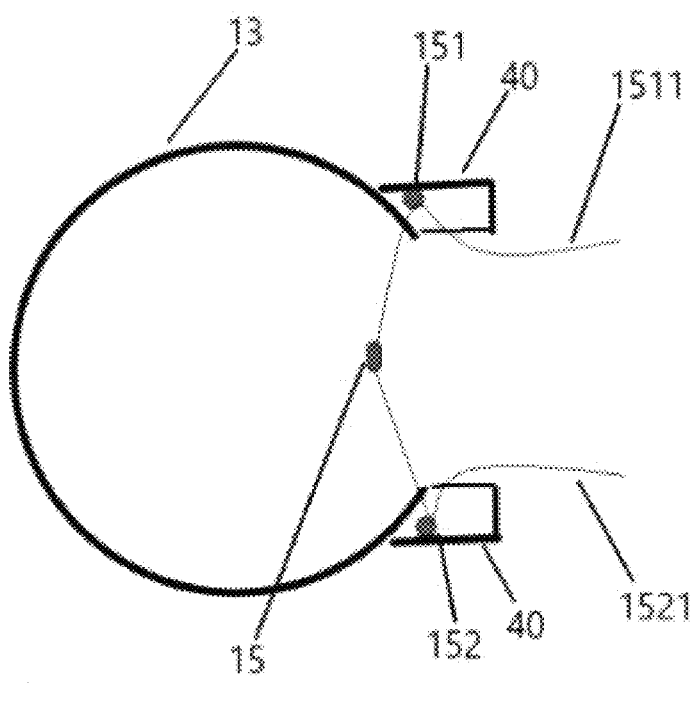
FIG. 19 is a schematic diagram of a third wrist joint transmission connection structure according to the embodiment of the present invention.

As shown in FIG. 19, according to the embodiment of the present invention, a main structure of a wrist joint 10 can comprise can comprise a shell 13, a fifth anchorage 15, a first steering wheel 151, a twelfth wire rope 1511, a second steering wheel 152, and a thirteenth wire rope 1521. The shell 13 can be a spherical hollow shell structure, and the spherical hollow shell structure can be provided with a plurality of holes for installing fixed components or arranging transmission components. Wherein, the fifth anchorage 15 can be arranged on a left or right side of a near end of the shell 13, the first steering wheel 151 can be arranged on an upper side of a first flange 40, the second steering wheel 152 can be arranged on a lower side of the first flange 40, and a far end of the twelfth wire rope 1511 can be fixedly connected with the fifth anchorage 15, bypassing an outer surface of the shell 13, passing through a hole of the first flange 40 and the first steering wheel 151 and connected with a power device of the surgical robot through transmission, a far end of the thirteenth wire rope 1521 can be fixedly connected to the fifth anchorage 15, bypasses an outer surface of the shell 13, passes through the hole of the first flange 40 and the second steering wheel 152, and is connected with the power device of the surgical robot. When the power device of the surgical robot starts to pull the twelfth wire rope 1511, loosen the thirteenth wire rope 1521, and the shell 13 rotates clockwise relying on the first flange 40, then the wrist joint 10 rotates clockwise. When the power device of the surgical robot starts to pull the thirteenth wire rope 1521, loosen the twelfth wire rope 1511, and the shell 13 rotates counterclockwise relying on the first flange 40, then the counterclockwise wrist rotation of the wrist joint 10 can be achieved.

It should be noted that the fifth anchorage 15 can be set as two, which are respectively fixed to connect the twelfth wire rope 1511 and the thirteenth wire rope 1521. A specific layout position of the two fifth anchorages 15 can be adjusted according to needs to achieve greater effect of rotating the wrist joint 10.

Figure 21:
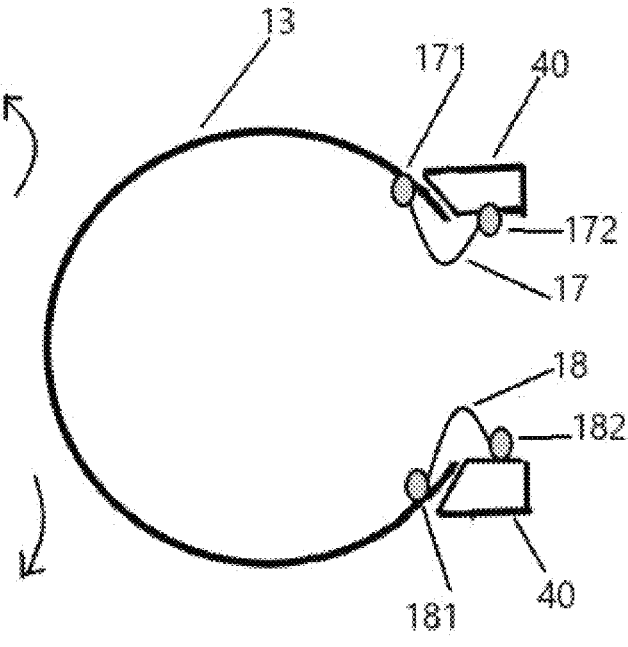
FIG. 21 is another schematic diagram of a spherical wrist joint and a first flange sliding connection structure according to the embodiment of the present invention.

As shown in FIG. 21, according to the embodiment of the present invention a main structure of a wrist joint 10 can comprise a shell 13, a sixth anchorage 171, a first cable chain 17, a seventh anchorage 172, an eighth anchorage 181, a second cable chain 18, and a ninth anchorage 182, wherein the sixth anchorage 171 can be arranged on an inner wall of the shell 13, and the seventh anchorage 172 can be arranged on an inner wall of a first flange 40, connected by the first cable chain 17, the eighth anchorage 181 can be arranged on an inner wall of the shell 13, and the ninth anchorage 182 can be arranged on an inner wall of the first flange 40, which is connected by the second cable chain 18. The first cable chain 17 and the second cable chain 18 can be made of elastic materials, so that the main structure of the wrist joint 10 and the first flange 40 can form a stable connection that can rotate and slide within a certain range.

It should be noted that two solid connection units are taken as an example between the main structure of the wrist joint 10 and the first flange 40 as shown in FIG. 21. In fact, one or more than two solid connection units can be set as required.

Figure 20:
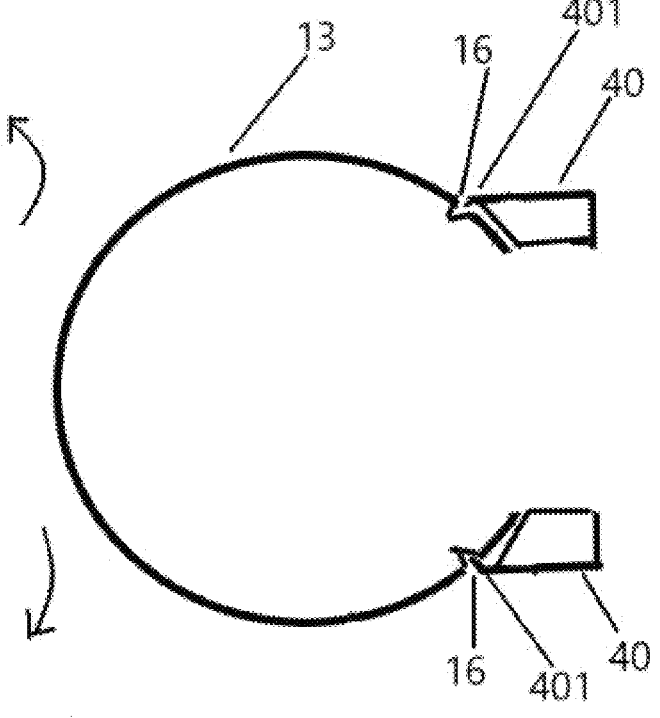
FIG. 20 is a schematic diagram of a spherical wrist joint and a first flange sliding connection structure according to the embodiment of the present invention.

In addition, as shown in FIG. 20, according to the embodiment of the present invention, another main structure of a wrist joint 10 can comprise a shell 13, a groove 16, and a convex shaft 401. The groove 16 can arranged around a rear end of the shell 13, the convex shaft 401 can be arranged at a far end of a first flange 40, and the convex shaft 401 can be a plurality of discontinuous structures. The convex shaft 401 can connected with the groove 16 in a sliding way, so that when the wrist joint 10 rotates, the main structure of the wrist joint 10 and the first flange 40 form a stable connection that can rotate and slide within a certain range.

Figure 22:
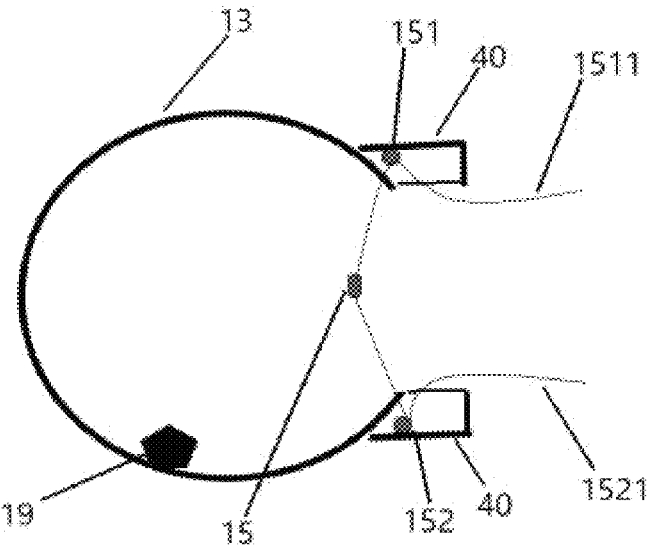
FIG. 22 is a structural diagram of a wrist joint as described in FIG. 1 including a gyroscope according to the embodiment of the present invention.

As shown in FIG. 22, according to the embodiment of the present invention another main structure of a wrist joint 10 can comprise a shell 13 and a gyroscope 19. The gyroscope 19 can be arranged inside the shell 13 configured to collect displacement data of the wrist joint 10, thereby tracking and recording a trajectory of a fetus movement.

An embodiment of the present invention provides a mechanical arm for fetal intrauterine positioning and fixation, which can comprise a host mechanical arm, a first auxiliary mechanical arm, and a second auxiliary mechanical arm.

Figure 23:
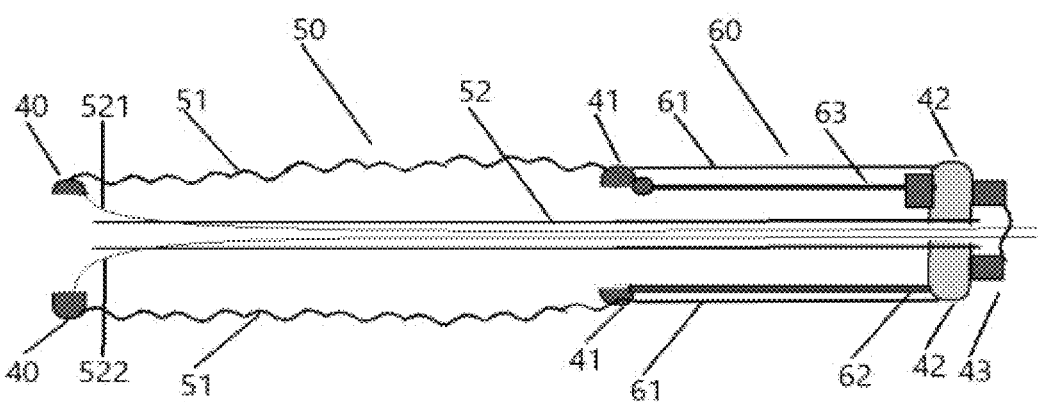
FIG. 23 is a structural diagram of a main mechanical arm including an intra amniotic segment mechanical arm and an outer amniotic segment mechanical arm according to the embodiment of the present invention.
Figure 24:
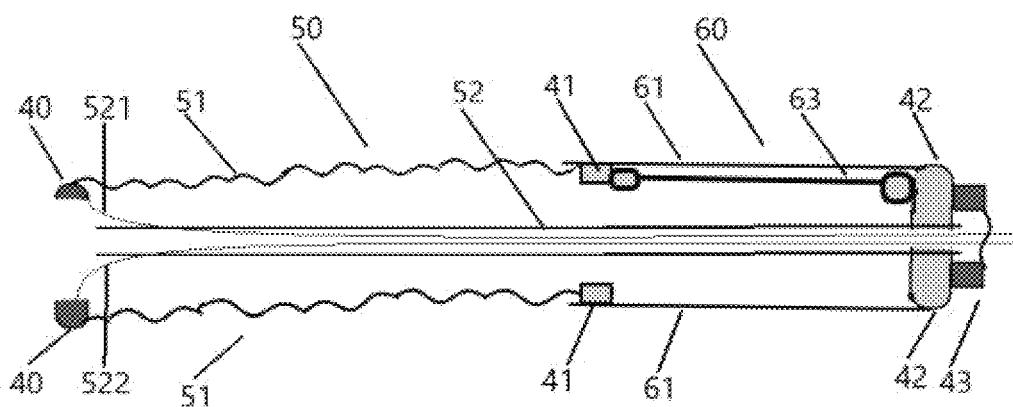
FIG. 24 is another structural diagram of a main mechanical arm including an intra amniotic segment mechanical arm and an outer amniotic segment mechanical arm according to the embodiment of the present invention.

Referring to FIGS. 23 and 24, according to the embodiment of the present invention a host mechanical arm can comprise an intra amniotic segment mechanical arm 50 and an outer amniotic segment mechanical arm 60, wherein a distal end of the intra amniotic segment mechanical arm 50 can be fixedly connected with a first flange 40, and a proximal end of the intra amniotic segment mechanical arm 50 can be connected in series with an outer amniotic segment mechanical arm 60 through a second flange 41, a distal end of the outer amniotic segment mechanical arm 60 can be connected in series with the intra amniotic segment mechanical arm 50 through the second flange 41, and a proximal end of the outer amniotic segment mechanical arm 60 can be connected with the surgical robot through a third flange 42 and an adapter 43.

As shown in FIG. 23, according to the embodiment of the present invention a intra amniotic segment mechanical arm 50 can comprise a first outer sleeve 51, an inner sleeve 52, a fourteenth wire rope 521, and a fifteenth wire rope 522, wherein the first outer sleeve 51 and the inner sleeve 52 can be made of flexible members (as an embodiment of the present invention, for the flexible members, see the structure with the patent application publication number of CN113598949A or the structure with the patent application publication number of CN113288440A) so that the intra amniotic segment mechanical arm 50 has a performance of a flexible mechanic. A far end of the fourteenth wire rope 521 can be fixedly connected with an upper end of a first flange 40, a near end of the fourteenth wire rope 521 can be threaded through the first outer sleeve 51, the inner sleeve 52 can be connected with a power device of a surgical robot, the fifteenth wire rope 522 can be fixedly connected with a lower end of the first flange 40, and a near end of the fifteenth wire rope 522 can be threaded through the first outer sleeve 51. The inner sleeve 52 can be connected with the power device of the surgical robot through transmission. When the power device of the surgical robot starts, the fourteenth wire rope 521 and the fifteenth wire rope 522 can be pulled at the same time, the first outer sleeve 51 can be shortened, and the intra amniotic segment mechanical arm 50 will be shortened accordingly, then a wrist joint 10 will be driven to retract through the first flange 40. On the contrary, when the power device of the surgical robot starts, the fourteenth wire rope 521 and the fifteenth wire rope 522 are loosened at the same time, the first outer sleeve 51 will be extended, the intra amniotic segment mechanical arm 50 extends correspondingly, and the wrist joint 10 can be driven to extend through the first flange 40.

When the power device of the surgical robot starts, if only the fourteenth wire rope 521 is pulled, the intra amniotic segment mechanical arm 50 will bow upward, if only the fifteenth wire rope 522 is pulled, the intra amniotic segment mechanical arm 50 will bow downward.

It can be understood that, as shown in FIG. 23, when a far end of the fourteenth wire rope 521 is fixedly connected with a left end of the first flange 40, and the fifteenth wire rope 522 is fixedly connected with a right end of the first flange 40, under the drive of a power device of the surgical robot, the intra amniotic segment mechanical arm 50 can arch to the left or right, so that in actual usage, the intra amniotic segment mechanical arm 50 can be attached to a maternal uterine wall to help build a surgical operation space, in order to avoid interference with an operation of a surgical manipulator.

As shown in FIG. 23, according to the embodiment of the present invention an outer amniotic segment mechanical arm 60 can comprise a second outer sleeve 61, a fixing rod 62, and a driving component 63, wherein the second outer sleeve 61 can be configured to wrap an internal structure of the outer amniotic segment mechanical arm 60, the fixing rod 62 can be connected with a second flange 41 and a third flange 42, configured to stabilize the structure of the outer amniotic segment mechanical arm 60, and the driving component 63 is electrically connected with a surgical robot, the second flange 41 can be driven to make the intra amniotic segment mechanical arm 50 rotate. It can be understood that the driving component 63 can use a motor to drive a transmission lever gear device to achieve a rotary driving effect.

In addition, as shown in FIG. 24, according to the embodiment of the present invention an intra amniotic segment mechanical arm 50 can also be partially penetrated into an outer amniotic segment mechanical arm 60. A driving component 63 can drive the intra amniotic segment mechanical arm 50 to perform rotary motion, and also drive the intra amniotic segment mechanical arm 50 to perform reciprocating motion. In practical application, the host mechanical arm can achieve greater reciprocating linear sliding and rotation, and achieve an effect of dragging the fetus in a large range.

Figure 25:
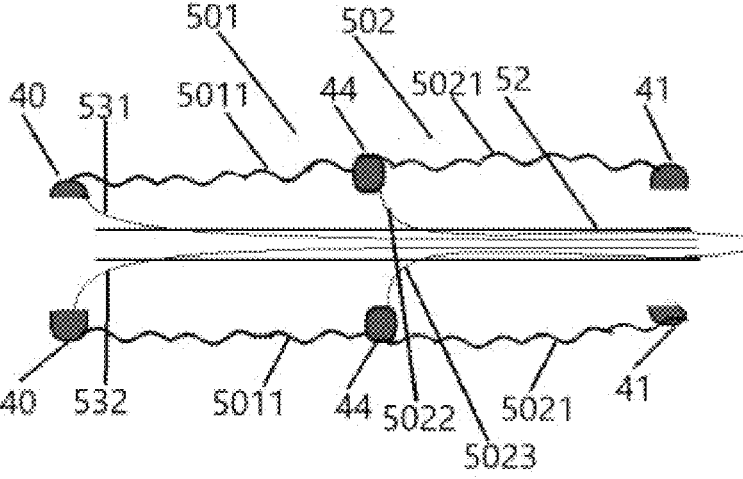
FIG. 25 is a structural diagram of the intra amniotic segment mechanical arm as described in FIGS. 23 and 24 including an inter arm joint according to the embodiment of the present invention.

In addition, an intra amniotic segment mechanical arm 50 can also be divided into a plurality of segments, which is equivalent to adding a plurality of elbow joints to the intra amniotic segment mechanical arm 50, so that the intra amniotic segment mechanical arm 50 can be more attached to a maternal uterine wall. As shown in FIG. 25, according to the embodiment of the present invention an intra amniotic segment mechanical arm 50 can comprise a first intra amniotic segment mechanical arm 501 and the second intra amniotic segment mechanical arm 502. The first intra amniotic segment mechanical arm 501 and the second first intra amniotic segment mechanical arm 502 can be connected in series through a fourth flange 44. The first intra amniotic segment mechanical arm 501 can comprise a third outer sleeve 5011, an inner sleeve 52, a sixteenth wire rope 531, and a seventeenth wire rope 532, wherein, the third outer sleeve 5011 can be made of flexible materials (as an embodiment of the present invention, the flexible member is shown in the structure with patent application publication number CN113598949A or the structure with patent application publication number CN113288440A), so that the first intra amniotic segment mechanical arm 501 has flexible mechanical arm performance. A far end of the sixteenth steel wire rope 531 can be fixedly connected with an upper end of a first flange 40, a near end of the sixteenth steel wire rope 531 can be threaded through the inner sleeve 52 and is connected with a power device of a surgical robot, a far end of the seventeenth steel wire rope 532 can be fixedly connected with a lower end of the first flange 40, and a near end of the sixteenth steel wire rope 531 can be threaded through the inner sleeve 52 and is connected with the power device of the surgical robot. The second first intra amniotic segment mechanical arm 502 can comprise a fourth outer sleeve 5021, an inner sleeve 52, an eighteenth wire rope 5022, and a nineteenth wire rope 5023, wherein the fourth outer sleeve 5021 can be made of flexible material (as an embodiment of the present invention, the flexible component is shown in the structure with the patent application publication number of CN113598949A or the structure with the patent application publication number of CN113288440A), so that the second intra amniotic segment mechanical arm 502 has a performance of flexible mechanical arm. A far end of the eighteenth wire rope 5022 can be fixedly connected with an upper end of the fourth flange 44. A near end of the eighteenth wire rope 5022 can be threaded through the inner sleeve 52 and is connected with the power device of the surgical robot. A far end of the nineteenth wire rope 5023 can be fixedly connected with a lower end of a fourth flange 44. A near end of the nineteenth wire rope 5023 can be threaded through the inner sleeve 52 and is connected with the power device of the surgical robot. When the power device of the surgical robot receives the command, and can drive the sixteenth wire rope 531, the seventeenth wire rope 532, the eighteenth wire rope 5022, and the nineteenth wire rope 5023 to achieve an upward or downward bow of the first intra amniotic segment mechanical arm 501 or the second intra amniotic segment mechanical arm 502, so that the intra amniotic segment mechanical arm 50 can be better attached to a maternal uterine wall in practical application, and help to build a better surgical operation space.

An embodiment of the present invention provides a first auxiliary mechanical arm. The first auxiliary mechanical arm can use a flexible mechanical arm or a rigid mechanical arm. The first auxiliary mechanical arm can include three or four degrees of freedom, including at least one degree of freedom of rotation. An end actuator of the first auxiliary mechanical arm can be a suction cup 70, configured to enter a amniotic cavity through a vaginal cervical fetal membrane channel or abdominal wall uterine fetal membrane channel to coordinate with a host mechanical arm and/or a manipulator perform fetal position adjustment.

Figure 26A:
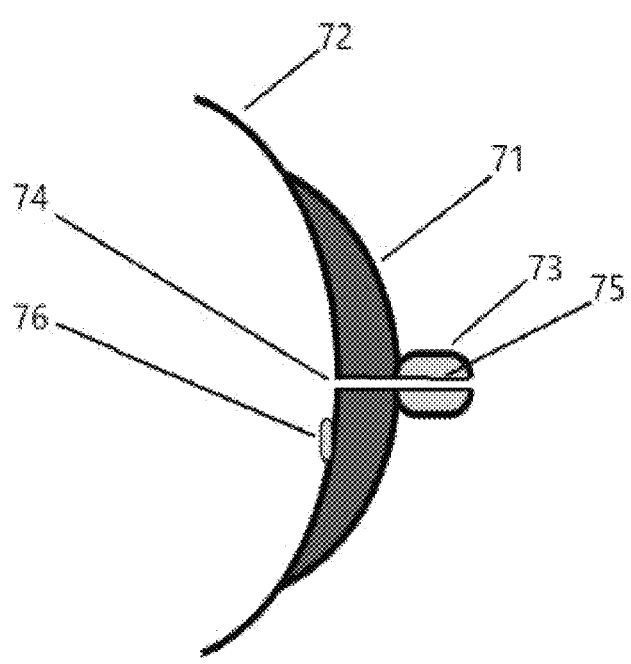
FIG. 26A is a schematic diagram of a sectional structure of a suction cup according to the embodiment of the present invention.
Figure 26B:
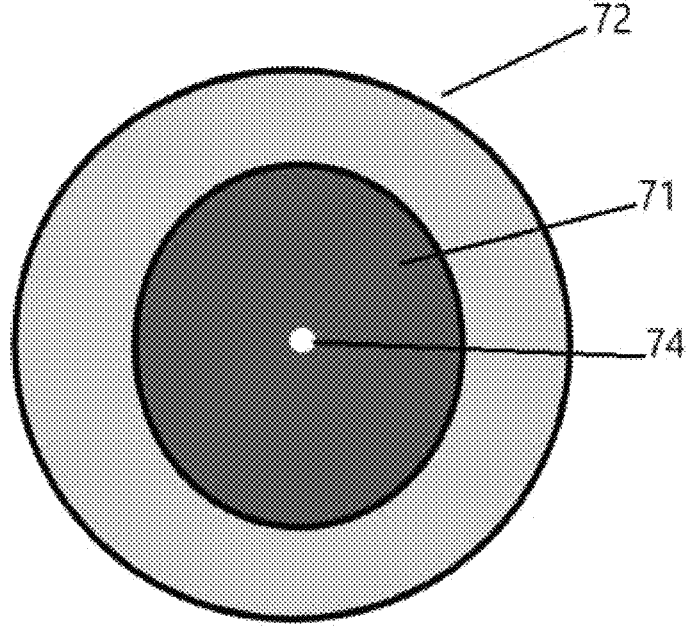
FIG. 26B is a schematic diagram of an adsorption surface of the suction cup as described in FIG. 26A according to the embodiment of the present invention.

As shown in FIGS. 26A and 26B, according to the embodiment of the present invention a suction cup 70 can comprise a disc body 71, a disc edge 72, an air vent 74, a mounting joint 73, an air passage 75, and a sensor 76, wherein, the disc body 71 can be a concave structure with a thick center and a thin edge, which can be made of highly elastic materials such as silica gel, with a diameter of no more than 5 mm, the center of the concave structure can be an air vent 74, and a periphery of the concave structure can be a disc edge 72, the disc edge 72 can be made of highly elastic materials such as silica gel, with a thickness of no more than 1 mm. The mounting joint 73 can be arranged on a convex side of the disc body 71 to connect a first auxiliary mechanical arm. The sensor 76 can be arranged on the concave side of the disc body 71 to collect a pressure data between the disc body 71 and the fetus. The vent 74 can be arranged in the mounting joint 73 and the air path 75 of the first auxiliary mechanical arm to connect with an air pump of a surgical robot, and the air pump can be electrically connected with a controller. The air pump of the surgical robot receives a command of the controller and can pump air, and then a negative pressure can be generated between the disc body 71, disc edge 72 and the fetus trunk or limb, the first auxiliary mechanical arm can drive the fetus to adjust a fetal position through the suction cup 70. When an air pumping is stopped and the negative pressure between the disc body 71, disc edge 72 and the fetus trunk or limb disappears, the first auxiliary mechanical arm can release the fetus through the suction cup 70. By analyzing the pressure data collected by the sensor 76, a system judges the negative pressure value between the disc body 71, disc edge 72 and the fetus trunk or limb. When the negative pressure value exceeds a preset range, the controller adjusts the negative pressure between the disc body 71, disc edge 72 and the fetus trunk or limb through the air pump to avoid damaging the fetus.

An embodiment of the present invention provides a second auxiliary mechanical arm. The second auxiliary mechanical arm can use a flexible mechanical arm or a rigid mechanical arm. The second auxiliary mechanical arm can include three or four degrees of freedom, including at least one degree of freedom of rotation. The second auxiliary mechanical arm can be configured to hold a camera, which can enter a amniotic cavity through a vaginal cervical fetal membrane channel or abdominal uterine fetal membrane channel, collect and transmit visible light, infrared light Radar, ultrasound and other image signals, provide image data for a doctor when he or she use a main mechanical arm, manipulator and a first auxiliary mechanical arm to perform fetal positioning.

An embodiment of the present invention provides a surgical robot for fetal intrauterine positioning and fixation, which can comprise an aforementioned main mechanical arm and manipulator for fetal intrauterine positioning and fixation, a second auxiliary mechanical arm and suction cup, a second auxiliary mechanical arm and camera, and a surgical robot body. The surgical robot body can comprise a power device, an air pump, an injection pump, a control processor, a drive device, a base, and a box. The surgical robot body can be a commercial surgical robot, such as the da Vinci surgical robot system of the Intuitive Surgical. The main mechanical arm and manipulator, the second auxiliary mechanical arm and suction cup, the second auxiliary mechanical arm and camera can be connected with the da Vinci surgical robot system through transmission and electrical connection, with a master slave operation mode, or a doctor remotely or near operating table controls the main mechanical arm and manipulator, the second auxiliary mechanical arm and suction cup, and the second auxiliary mechanical arm and camera implement fetal positioning and fixation.

An embodiment of the present invention provides a handle for fetal intrauterine positioning fixation. The handle can be connected with the main mechanical arm, the first auxiliary mechanical arm and the second auxiliary mechanical arm through transmission. A doctor can operate the main mechanical arm, the first auxiliary mechanical arm and the second auxiliary mechanical arm through the handle, which is used to connect the main mechanical arm and the mechanical arm, the first auxiliary mechanical arm and the suction cup, the second auxiliary mechanical arm and camera enter an amniotic cavity through a vaginal cervical fetal membrane pathway or an abdominal wall uterine fetal membrane pathway, implement fetal positioning and body position fixation, and construct an operation space for fetal intrauterine surgery.

Figure 27:
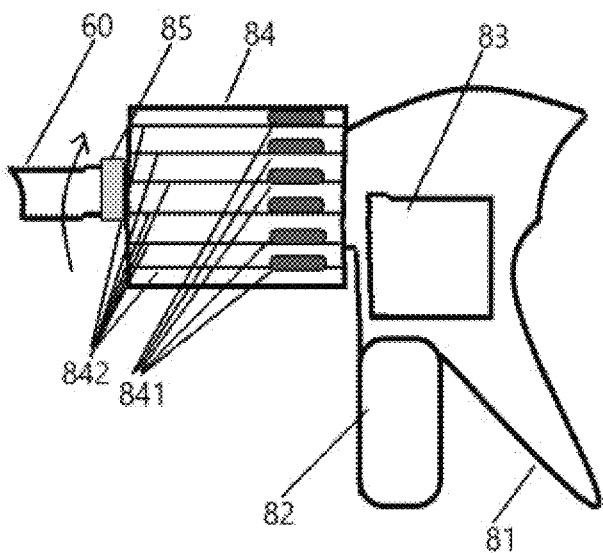
FIG. 27 is a schematic diagram of a handle according to the embodiment of the present invention.

Referring to FIG. 27, according to the embodiment of the present invention a handle can comprise a press switch 81, a hand piece 82, a control panel 83, a drive box 84, and a connection component 85. Among them, the connecting component 85 can be used to connect an outer amniotic segment mechanical arm 60 with the handle. The driving box 84 can include a plurality of driving motors 841 and a plurality of driving steel wire ropes 842. The driving motor 841 is electrically connected with the control panel 83. The driving motor 841 can be powered by an external power supply. The driving steel wire rope 842 can be correspondingly connected with a steel wire rope of a main mechanical arm and a manipulator. The control panel 83 can use touch screen, voice and other human-machine interaction modes to facilitate doctors to give instructions, operate the drive motor 841, the main mechanical arm and the manipulator.

In addition, the doctor can operate the drive motor 841 by pressing the switch 81. The doctor can hold the hand piece 82 with one hand and operate the press switch 81 with the other hand. Of course, the hand piece 82 can also be fixed on the mobile support to reduce a burden on the doctor.

In addition, as shown in FIG. 27, the connecting member 85 can also be fixed on the support to increase stability during operation.

It can be understood that a handle in the embodiment of the present invention can also be connected to a second auxiliary mechanical arm configured to manually control a camera to collect maternal uterus and intrauterine fetal image data, and can also be connected to a first auxiliary mechanical arm configured to manually control a first auxiliary mechanical arm and sucker, and adjust a fetal position.

An embodiment of the present invention provides a fetal intrauterine positioning and fixation system, which can comprise an operating system, a control system, and a positioning and navigation system. The control system can comprise an image processing software module, a surgery planning software module, a manipulator control module, and a fetal motion trajectory module. The positioning and navigation system can comprise an imaging module, a tracking module, and a display module. According to images imported before a surgery, a dynamic three-dimensional model is formed. The three-dimensional model can be unified with an actual body position of the fetus and mother, a real-time position of a manipulator in space, and a suction cup in the same coordinate system. A three-dimensional positioning system can be used to collect and display a position of the manipulator and suction cup in real time in space. A doctor adjusts and fixes the position of the fetus by observing a corresponding position relationship between the manipulator, suction cup and the pathological position of the fetus in the three-dimensional model, and constructs the surgical treatment space.

In addition, ultrasonic detection data should be collected before an operation, such as uterine shape, thickness of uterine wall, length of cervix, thickness and aperture of cervical tube wall, fetal size, fetal lesion site, predetermined surgical site, fetal relative position in a mother, fetal membrane thickness, placental location and placental area, umbilical cord position, umbilical cord length, amniotic fluid volume, etc., and channel type should be selected. On this basis, an algorithm should plan a best path, which can guide a doctor to operate a main mechanical arm, a first auxiliary mechanical arm, and a second auxiliary mechanical arm along a desired path to simulate a position, force, torque action distance, and rotation angle of a fetal body and/or limb, so as to achieve accurate positioning and fixation effect. Especially for cases with complex fetal conditions, preoperative doctors can conduct simulation exercises in advance, and optimize the algorithm when necessary to obtain better implementation effect. In addition, if multiple births are treated surgically, preoperative planning can also help improve the implementation effect and avoid mistakes.

As shown in FIGS. 28 to 33, an embodiment of the present invention provides a method of fetal intrauterine positioning and fixation. A one-bore surgical robot scheme for entering an amniotic cavity through a vagina, cervix and fetal membrane adjusts and fixes a fetal position, and constructs a surgical treatment space. The process 100 can comprise a plurality of steps as fellow.

S110: Plan a fetal intrauterine positioning and fixation path. Ultrasonic inspection data before operation can be collected, and a plurality of best paths including a main mechanical arm path, a manipulator path, a first auxiliary mechanical arm path, a second auxiliary mechanical arm path, and a handle and/or surgical robot path can be planned, and a plurality of parameters including control and clamping position, force, torque action distance, rotation angle, etc. in a specific operation process can be proposed.

S120: Create a passage through vagina, cervix and fetal membrane into amniotic cavity.

Figure 28:
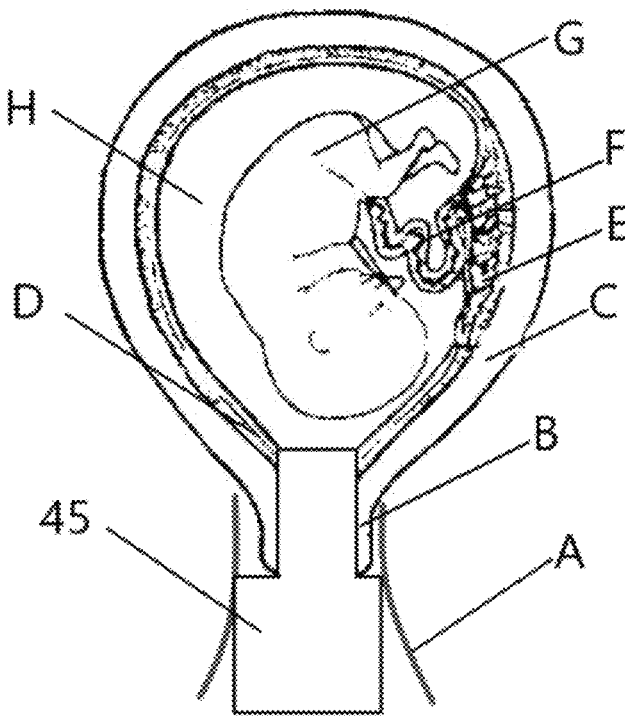
FIG. 28 is a schematic diagram of a positional relationship among a mother, a vaginal passage device and a fetus according to the embodiment of the present invention.

As shown in FIG. 28, after a vagina (shown as A) and a cervix (shown as B) are expanded, an ultrasound equipment can be used to detect a uterus (shown as C), a fetal membrane (shown as D), a placenta (shown as E), an umbilical cord (shown as F), and a fetus (shown as G). Under a guidance of ultrasound, a transvaginal access device 45 can be inserted through the vagina, the cervix, and the fetal membrane, a front end of the transvaginal access device 45 can enter a amniotic cavity (shown as H), and a rear end of the transvaginal access device 45 can be located at an outer opening of vagina A.

Figure 29:
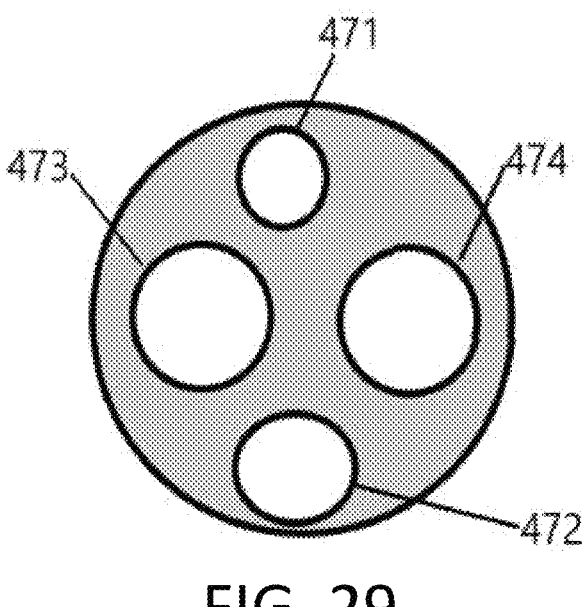
FIG. 29 is a schematic diagram of an intrathecal foramen structure of the vaginal passage device as described in FIG. 28 according to the embodiment of the present invention.

As shown in FIG. 29, an intrathecal hole of a transvaginal access device 45 can comprise a plurality of operation holes, and the operation holes can comprise an upper operation hole 471, a lower operation hole 472, a left operation hole 473, and a right operation hole 474, which can be respectively configured to insert a main mechanical arm, a manipulator, a first auxiliary mechanical arm and suction cup, a second auxiliary mechanical arm and camera, a surgical arm, and/or a hand piece of a therapy apparatus. It should be noted that when an intrauterine fetus is positioned and fixed, three of the operation holes need to be used to insert a host mechanical arm and manipulator, the first auxiliary mechanical arm and suction cup, the second auxiliary mechanical arm and camera. After the intrauterine fetus is positioned and fixed, the first auxiliary mechanical arm and suction cup can be withdrawn, and two operation holes can be used to insert two sets of surgical manipulators and surgical treatment instruments to coordinate an implementation of surgical treatment.

Figure 30:
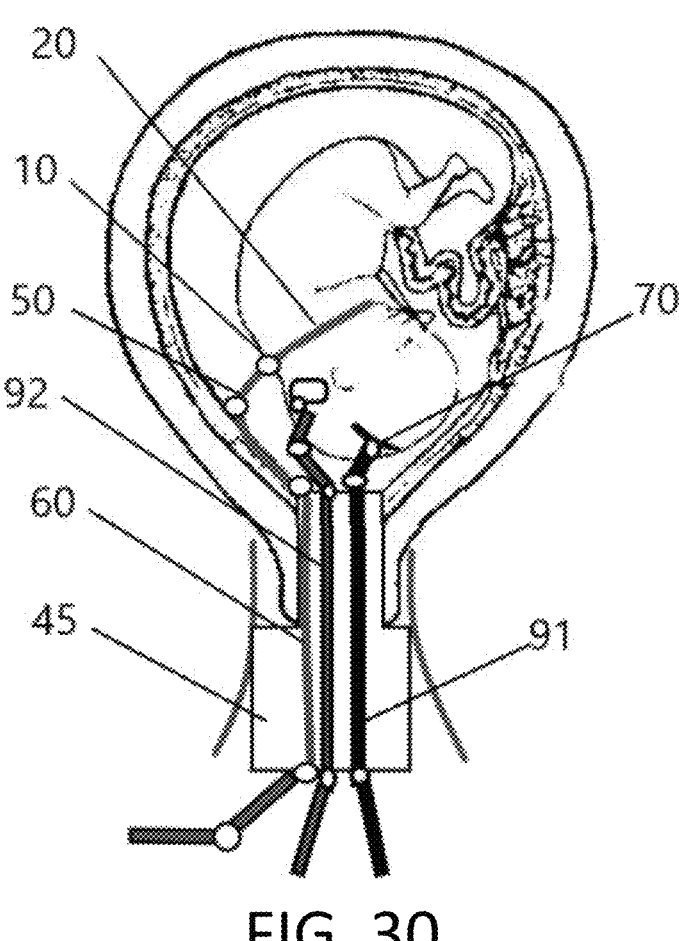
FIG. 30 is a schematic diagram of a position relationship between a mechanical arm trans-vaginal passage and a fetus according to the embodiment of the present invention.

S130: Insert the second auxiliary mechanical arm and camera. As shown in FIGS. 28 and 30, a second auxiliary mechanical arm 92 and a camera can be inserted into the amniotic cavity through the transvaginal access device 45 in step S120 under the guidance of ultrasound. The second auxiliary mechanical arm 92 can be connected with an adapter, and then connected with a surgical robot body or a handle to collect image data.

S140, Insert a first auxiliary mechanical arm and a suction cup. As shown in FIGS. 28 and 30, a first auxiliary mechanical arm 91 and a suction cup 70 can be inserted into the amniotic cavity under ultrasound guidance through the transvaginal access device 45 in step S120. The first auxiliary mechanical arm 91 can be connected with an adapter, and then connected with the surgical robot body or handle. The first auxiliary mechanical arm 91 and suction cup 70 can be controlled visually to push the fetus, so that a space for accommodating a first finger 20, a wrist joint 10 and a mechanical arm 50 in the amniotic cavity can be constructed.

S150: Insert a main mechanical arm and a manipulator. Specifically, as shown in FIGS. 28 and 30, a first finger 20, a wrist joint 10, an intra amniotic segment mechanical arm 50 and an outer amniotic segment mechanical arm 60 can be inserted into a space made in step S140 through the transvaginal access device 45 of step S120, and then connected with an adapter, and then a surgical robot body or a handle.

S160: Position a fetus. According to a fetal dynamic image data in the amniotic cavity collected in step S130 and immediate ultrasonic inspection data, an intrauterine positioning and fixation path of the fetus planned in step S110 can be updated in real time. A doctor can control the first auxiliary mechanical arm 91 and the suction cup 70, a host mechanical arm and a auxiliary mechanical arm to push, pull, flip, and drag the fetus position by referring to an intrauterine positioning and fixation path of the fetus. The position of the fetus for scheduled surgical treatment is fully exposed in a vaginal cervical fetal membrane amniotic cavity pathway created in step S120.

It should be noted that the fetal intrauterine positioning and fixation path can include avoiding a possible interference of an umbilical cord, a first application point and torque as well as an operating distance and rotation angle, a second application point and torque as well as an operating distance and rotation angle, a third application point and torque as well as an operating distance and rotation angle, a fetal trunk and/or limb manipulator clamping or suction cup adsorption position and strength, so as to guide an operator to implement the mechanical arm, the manipulator and the suction cup cooperatively.

Figure 31:
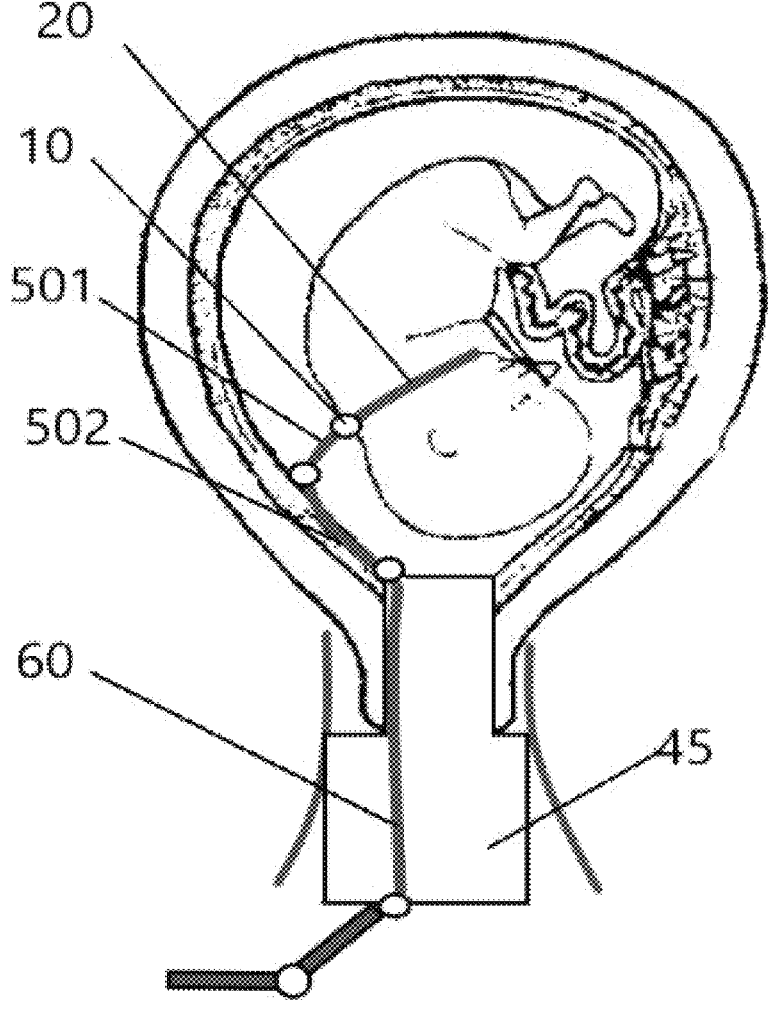
FIG. 31 is a schematic diagram of a main machine arm and manipulator through a vaginal passage fixing a fetus body according to the embodiment of the present invention.

S170: Withdraw the first auxiliary machine arm and suction cup, and fix a fetal position. As shown in FIG. 31, after the first auxiliary mechanical arm and suction cup are withdrawn, a manipulator can hold the fetal trunk and/or limb, and an intra amniotic segment manipulator 502 can be attached to a uterine wall to construct a operation space. At the same time, a sensor set on a first finger 20 can collect fetal physiological data configured for real time reference, and pressure data configured to judge strength of the manipulator for holding the fetal trunk and/or limb.

Figure 32:
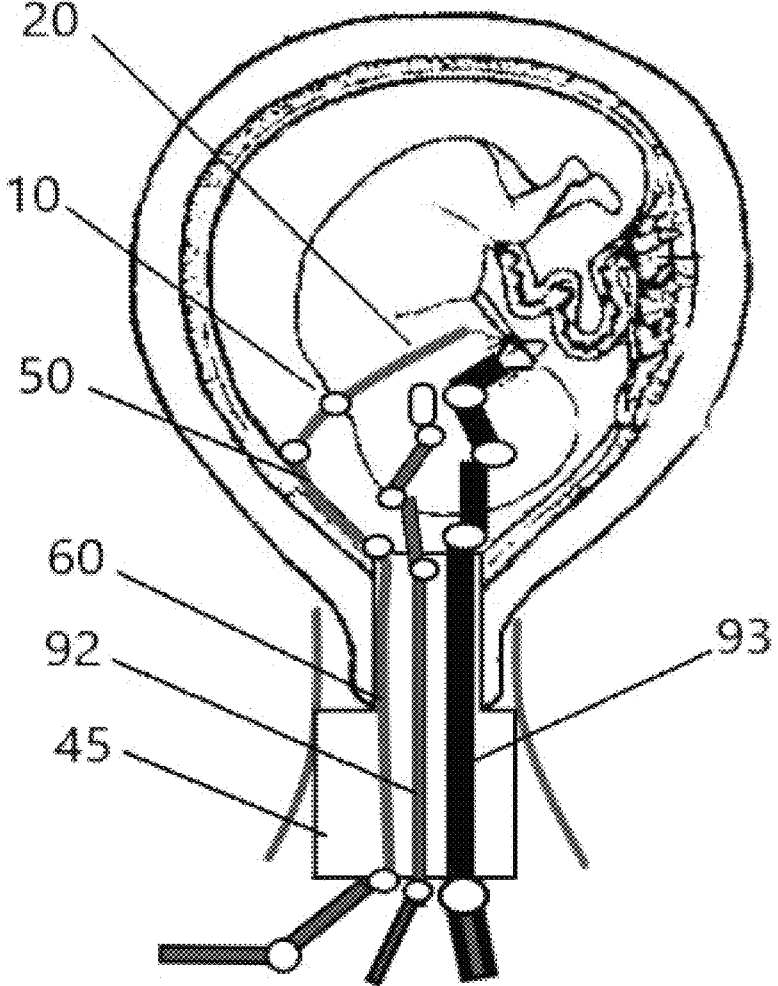
FIG. 32 is another schematic diagram of a position relationship between a mechanical arm trans-vaginal passage and a fetus according to the embodiment of the present invention.

S180: Dynamic adjust fetal position during operation. As shown in FIGS. 28 and 32, the manipulator 93 and surgical instruments can be inserted into the amniotic cavity through the transvaginal access device 45 in step S120 to perform surgical treatment.

During an operation, if the fetal position needs to be adjusted, a first finger 20, a wrist joint 10, an intra amniotic segment mechanical arm 50 and an outer amniotic segment mechanical arm 60 can be manipulated to adjust the fetal position in real time.

S190: After the operation, release the fetus by the main mechanical arm and manipulator and withdraw.

As a feasible scheme, a one-bore surgical robot and surgical treatment instruments can enter an amniotic cavity through an abdominal wall fetal membrane to adjust and fix the fetal position, build a surgical treatment space, and perform surgical treatment.

As a feasible scheme, a one-bore surgical robot can also be replaced with a handle to connect a mechanical arm, so that an endoscopic surgery scheme can be configured to adjust and fix the fetus position, build a surgical treatment space, and perform surgical treatment.

As shown in FIGS. 28 to 36, the embodiment of the present invention provides another method of fetal intrauterine positioning and fixation, which is used to adjust and fix a position of a fetus in a two-bore surgical robot scheme for entering a amniotic cavity through a vaginal cervix fetal membrane and an abdominal wall uterine fetal membrane, and to construct a surgical treatment space. The process 200 can comprise a plurality of steps as fellow.

S210: Plan a fetal intrauterine positioning and fixation path. Ultrasonic inspection data before operation can be collected, and a plurality of best paths including a main mechanical arm path, a manipulator path, a first auxiliary mechanical arm path, a second auxiliary mechanical arm path, and a handle and/or surgical robot path can be planned, and a plurality of parameters including control and clamping position, force, torque action distance, rotation angle, etc. in a specific operation process can be proposed.

S220: Create access to an amniotic cavity through a vagina, cervix and fetal membrane or abdominal wall, uterus and fetal membrane.

Figure 34:
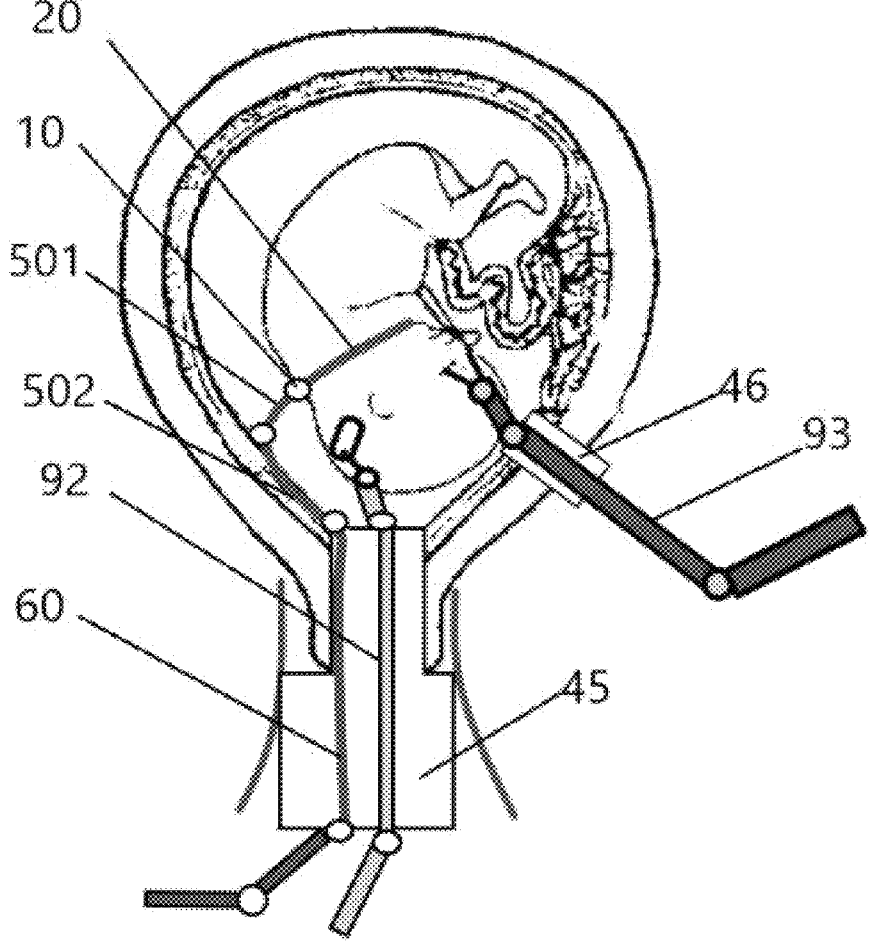
FIG. 34 is a schematic diagram of a position relationship between a mechanical arm of trans-vaginal passage, a mechanical arm trans-abdominal passage and a fetus according to the embodiment of the present invention.

As shown in FIGS. 28 and 34, under ultrasound guidance, a transvaginal access device 45 can be inserted through transvaginal (shown as A), cervix (shown as C) and fetal membrane (shown as D). A front end of the transvaginal access device 45 can enter into a amniotic cavity (shown as H), a rear end of the transvaginal access device 45 can be located at a outer opening of vagina (shown as A). Under ultrasound guidance, a transabdominal access device 46 can be led through an abdominal wall wound, uterine wall and fetal membrane channel. When making a transabdominal uterine fetal membrane passage, the transabdominal uterine fetal membrane passage must avoid a placenta. Furthermore, a preferred small incision can be performed at a belly button or paraumbilical approach. If the belly button or paraumbilical approach may damage the placenta, other areas of the abdomen should be selected.

Figure 35:
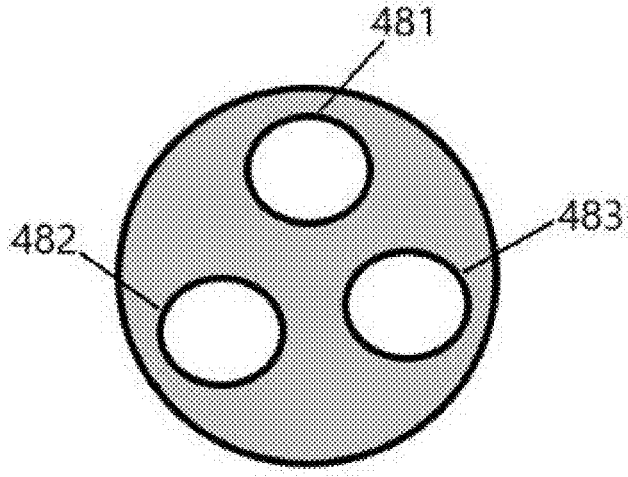
FIG. 35 is a schematic diagram of another intrathecal foramen structure of the vaginal passage device as described in FIG. 28 according to the embodiment of the present invention.

As shown in FIG. 35, an inner sheath hole of the transvaginal access device 45 can be divided into an upper operation hole 481, a lower left operation hole 482, and a lower right operation hole 483, which can be respectively configured to insert a main mechanical arm and manipulator, a first auxiliary mechanical arm and suction cup, a second auxiliary mechanical arm and camera. It should be noted that after an intrauterine fetal positioning and fixation is completed, the first auxiliary mechanical arm and suction cup can be withdrawn, and an empty operation hole can be used to insert a set of surgical mechanical arm and surgical treatment instruments, cooperate with the implementation of surgical treatment, or be used to establish a fetal life support system, such as artificial amniotic fluid circulation purification device, intravenous blood transfusion device, etc.

Figure 36:
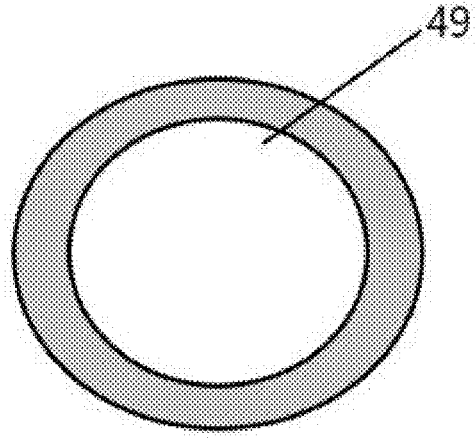
FIG. 36 is a schematic diagram of an intrathecal foramen structure of a trans-abdominal passage device according to the embodiment of the present invention.

As shown in FIG. 36, an intrathecal hole 49 of a transabdominal access device 46 can be used to insert surgical manipulators and surgical treatment instruments for surgical treatment. Of course, if it is possible to avoid damaging a placenta, an aperture of the transabdominal access device 46 can be appropriately increased, and a plurality of intrathecal holes 49 can be arranged for placing a plurality of surgical manipulators, surgical treatment instruments or other auxiliary devices to perform surgical treatment.

S230: Insert a second auxiliary mechanical arm and camera, a first auxiliary mechanical arm and suction cup, a main mechanical arm and manipulator in the same way as step S130, step S140 and step S150.

S240: Position, fix and dynamic adjust during a operation a fetus in the same way as step S160, S170, and S180.

S250: After an operation, release the fetus by the main mechanical arm and manipulator and withdraw.

The above description is only an example of the present invention, and does not limit the technical scope of the present invention. Therefore, any minor modification, equivalent change and modification of the above embodiments according to the technical essence of the present invention still fall within the scope of the technical solution of the present invention. Professionals should be aware that professionals can use different methods to achieve the described functions for each specific application, but such implementation should not be considered beyond the scope of this application.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A fetal intrauterine positioning fixation manipulator, entering an amniotic cavity through a vaginal cervical fetal membrane access and/or abdominal wall uterine fetal membrane access to adjust and fix a fetal position in a maternal uterus, comprising:

a wrist joint configured to flex, extend and/or rotate a plurality of finger wrist joints, a first finger configured to clamp and/or hold a fetus, the first finger being connected with a first finger wrist joint, and a second finger configured to clamp and/or hold the fetus and cooperate with the first finger, the second finger being connected with a second finger wrist joint;

wherein the finger wrist joint is connected with a mechanical arm through a steel wire rope threaded through the wrist joint, and a distal end of the wrist joint is detachably connected with the first finger and the second finger respectively;

wherein the first finger comprises a first arc rod, a first connecting tube, a first pull rod, and a second pull rod, the first arc rod and the first connecting tube is detachably connected, the first connecting tube, the first pull rod, and the second pull rod rotate around the first finger wrist joint, and the first connecting tube, the first pull rod and the second pull rod are fixedly connected with each other.

2. The fetal intrauterine positioning fixation manipulator according to claim 1, wherein the first pull rod is connected with a power device of a surgical robot through the first steel wire rope, and the third pull rod is connected with the power device of the surgical robot through the second steel wire rope, and there is an elastic strip between the second pull rod and the fourth pull rod.

3. The fetal intrauterine positioning fixation manipulator according to claim 1, wherein the first finger further comprises an air bag, wherein the air bag surrounds the first arc rod or an inner arc arranged on the first arc rod.

4. The fetal intrauterine positioning fixation manipulator according to claim 3, wherein the first finger further comprises a plurality of sensors, the sensors are arranged in the inner arc of the air bag.

5. A fetal intrauterine positioning fixation manipulator, entering an amniotic cavity through a vaginal cervical fetal membrane access and/or abdominal wall uterine fetal membrane access to adjust and fix a fetal position in a maternal uterus, comprising:

a wrist joint configured to flex, extend and/or rotate a plurality of finger wrist joints, a first finger configured to clamp and/or hold a fetus, the first finger being connected with a first finger wrist joint, and a second finger configured to clamp and/or hold the fetus and cooperate with the first finger, the second finger being connected with a second finger wrist joint;

wherein the second finger comprises a second arc rod, a second connecting tube, a third pull rod, and a fourth pull rod, the second arc rod and the second connecting tube is detachably connected, the second connecting tube, the third pull rod, and the fourth pull rod rotate around the second finger wrist joint, the second connecting tube, the third pull rod and the fourth pull rod are fixedly connected with each other.

6. The fetal intrauterine positioning fixation manipulator according to claim 5, wherein the second finger further comprises an air bag, the air bag surrounds the second arc rod or is arranged on an inner arc of the second arc rod.

7. A fetal intrauterine positioning fixation manipulator, entering an amniotic cavity through a vaginal cervical fetal membrane access and/or abdominal wall uterine fetal membrane access to adjust and fix a fetal position in a maternal uterus, comprising:

a wrist joint configured to flex, extend and/or rotate a plurality of finger wrist joints, a first finger configured to clamp and/or hold a fetus, the first finger being connected with a first finger wrist joint, and a second finger configured to clamp and/or hold the fetus and cooperate with the first finger, the second finger being connected with a second finger wrist joint;

wherein the wrist joint is connected with a first flange by sliding and rotating, the first flange is connected with an outer sleeve of a mechanical arm fixedly, and a power device of a surgical robot through a wire rope threaded through the mechanical arm;

wherein the wrist joint comprises a shell, a first anchorage, an eighth steel wire rope, a second anchorage, and a ninth steel wire rope, configured to realize an extension and flexion of the wrist joint.

8. The fetal intrauterine positioning fixation manipulator according to claim 7, wherein the wrist joint further comprises a fifth anchorage, a first steering wheel, a twelfth wire rope, a second steering wheel, and a thirteenth wire rope, configured to realize a movement of the wrist joint.

9. The fetal intrauterine positioning fixation manipulator according to claim 8, wherein the shell comprises a gyroscope configured to collect data of a wrist joint displacement track and a fetus movement track.

10. A fetal intrauterine positioning fixation mechanical arm, comprising:

a main mechanical arm configured to assist a manipulator to enter an amniotic cavity, implement fetal positioning and fixation, and build an operation space for fetal intrauterine surgery, the main mechanical arm being connected with the manipulator, and a surgical robot body or a handle, a first auxiliary mechanical arm configured to coordinate the main mechanical arm to enter the amniotic cavity for fetal position adjustment, and a second auxiliary mechanical arm configured to clamp and carry a camera into the amniotic cavity to collect image data;

wherein the main mechanical arm comprises an intra amniotic segment mechanical arm and an outer amniotic segment mechanical arm, a distal end of the intra amniotic segment mechanical arm is fixedly connected with a first flange, a proximal end of the intra amniotic segment mechanical arm is connected in series with the outer amniotic segment mechanical arm through a second flange, and a proximal end of the outer amniotic segment mechanical arm is connected in series through a third flange and an adapter is connected with a handle or a surgical robot.

11. The fetal intrauterine positioning fixation mechanical arm according to claim 10, wherein the intra amniotic segment mechanical arm comprises a first outer sleeve, an inner sleeve, a fourteenth wire rope, and a fifteenth wire rope, a distal end of the fourteenth wire rope is fixedly connected with an upper end of a first flange, and a proximal end of the fourteenth wire rope is threaded through the first outer sleeve and the inner sleeve connected with a power device of a surgical robot through transmission, the fifteenth steel wire rope is fixedly connected with a lower end of the first flange, and a near end of the fifteenth steel wire rope passes through the first outer sleeve and the inner sleeve transmission connected with the power device of the surgical robot.

12. The fetal intrauterine positioning fixation mechanical arm according to claim 11, wherein the intra amniotic segment mechanical arm is partially penetrated into the outer amniotic segment mechanical arm, so that the outer amniotic segment mechanical arm drives the intra amniotic segment mechanical arm to rotate, and reciprocate.

13. The fetal intrauterine positioning fixation mechanical arm according to claim 10, wherein the outer amniotic segment mechanical arm comprises a second outer sleeve, a fixing rod, and a driving component, the second outer sleeve is configured to wrap an inner structure, the fixing rod is connected with a second flange and a third flange configured to stabilize the outer amniotic segment mechanical arm, and the driving component is electrically connected with a surgical robot the robot configured to drive the second flange to make the outer amniotic segment mechanical arm rotate.

14. A fetal intrauterine positioning fixation mechanical arm, comprising:

a main mechanical arm configured to assist a manipulator to enter an amniotic cavity, implement fetal positioning and fixation, and build an operation space for fetal intrauterine surgery, the main mechanical arm being connected with the manipulator, and a surgical robot body or a handle, a first auxiliary mechanical arm configured to coordinate the main mechanical arm to enter the amniotic cavity for fetal position adjustment, and a second auxiliary mechanical arm configured to clamp and carry a camera into the amniotic cavity to collect image data;

wherein the first auxiliary mechanical arm comprises a suction cup configured to adsorb a fetus, wherein the suction cup comprises a disc body, a disc edge, a vent hole, a mounting joint, an air path, and a sensor, a center of the disc body is the vent hole, the mounting joint is configured to connect the first auxiliary mechanical arm, the sensor is arranged on the disc body to collect pressure data between the disc body and the fetus, and the vent hole is connected with an air pump of a surgical robot through an air path, the air pump is electrically connected with a control processor.

* * * * *